(12) United States Patent
Pellicciari et al.

(10) Patent No.: US 11,034,717 B2
(45) Date of Patent: Jun. 15, 2021

(54) FARNESOID X RECEPTOR MODULATORS

(71) Applicant: Intercept Pharmaceuticals, Inc., New York, NY (US)

(72) Inventors: Roberto Pellicciari, Perugia (IT); Antimo Gioiello, Perugia (IT)

(73) Assignee: Intercept Pharmaceuticals, Inc., New York, NY (US)

( * ) Notice: Subject to any disclaimer, the term of this patent is extended or adjusted under 35 U.S.C. 154(b) by 0 days.

(21) Appl. No.: 15/288,390

(22) Filed: Oct. 7, 2016

(65) Prior Publication Data

US 2017/0101434 A1 Apr. 13, 2017

Related U.S. Application Data

(60) Provisional application No. 62/238,246, filed on Oct. 7, 2015.

(51) Int. Cl.
| | | |
|---|---|---|
| *C07J 43/00* | (2006.01) | |
| *C07J 41/00* | (2006.01) | |
| *C07J 9/00* | (2006.01) | |
| *C07J 31/00* | (2006.01) | |
| *C07J 71/00* | (2006.01) | |

(52) U.S. Cl.
CPC .............. *C07J 43/003* (2013.01); *C07J 9/00* (2013.01); *C07J 9/005* (2013.01); *C07J 31/006* (2013.01); *C07J 41/0083* (2013.01); *C07J 41/0055* (2013.01); *C07J 41/0061* (2013.01); *C07J 41/0094* (2013.01); *C07J 71/001* (2013.01)

(58) Field of Classification Search
CPC ..................................................... C07J 43/003
See application file for complete search history.

(56) References Cited

U.S. PATENT DOCUMENTS

| | | | |
|---|---|---|---|
| 2,599,481 A | 6/1952 | Plattner et al. | |
| 4,514,393 A * | 4/1985 | Castagnola | C07J 9/005 |
| | | | 514/178 |
| 9,611,289 B2 * | 4/2017 | Pellicciari | C07J 9/005 |
| 10,047,117 B2 | 8/2018 | Steiner et al. | |
| 10,532,061 B2 * | 1/2020 | Pellicciari | A61P 1/16 |
| 2010/0093687 A1 | 4/2010 | Song et al. | |
| 2010/0152151 A1 * | 6/2010 | Pellicciari | C07J 9/00 |
| | | | 514/182 |
| 2012/0283234 A1 | 11/2012 | Pellicciari et al. | |
| 2014/0371190 A1 | 12/2014 | Pellicciari | |
| 2016/0014529 A1 | 1/2016 | Hecht et al. | |
| 2016/0145295 A1 * | 5/2016 | Or | C07J 41/0061 |
| | | | 514/176 |
| 2016/0145296 A1 * | 5/2016 | Or | C07J 43/003 |
| | | | 514/129 |

FOREIGN PATENT DOCUMENTS

| | | | |
|---|---|---|---|
| EP | 0312867 | 4/1989 | |
| WO | WO 2002/75298 | 9/2002 | |
| WO | WO-2014184271 A1 * | 11/2014 | .............. C07J 9/005 |
| WO | WO 2017/062763 A1 | 4/2017 | |
| WO | WO 2017/062856 | 4/2017 | |
| WO | WO 2017/156024 | 9/2017 | |

OTHER PUBLICATIONS

CAS Entry for International Application Publication No. WO 2004064521 A1 by Koga et al., 2004.*
SciFinder Record for Reiner et al. Monatschefte fuer Chemie 1975, 106, 1415-1428 (Year: 1975).*
CAS Registry Entry for Registry No. 163976-40-7, which entered STN on Jun. 22, 1995 (Year: 1995).*
Ishida et al. Biol. Pharm. Bull. 1999, 22, 828-835 (Year: 1999).*
CAS Registry Entry for Registry No. 203739-20-2, which entered STN on Apr. 7, 1998 (Year: 1998).*
CAPLUS record for Halperin, G. Steroids 1979, 33, 295-304 (Year: 1979).*
Turner et al. J. Biol. Chem. 1946, 166, 345-365 (Year: 1946).*
Bream et al. J. Chem. Soc. 1957, 1974-1981 (Year: 1957).*
Bidstrup, et al., "CYP2C8 and CYP3A4 are the principal enzymes involved in the human in vitro biotransformation of the insulin secretagogue repaglinide", *Br. J. Clin. Pharmacol.*, 2003, 56, 305-314.
Cree and Andreotti, "Measurement of Cytotoxicity by ATP-based Luminescence Assay in Primary Cell Cultures and Cell Lines", *Toxicology in-Vitro*, 1997, 11, 553-556.
Crouch, et al., "The use of ATP bioluminescence as a measure of cell proliferation and cytotoxicity", *J. Immunol. Methods*, 1993, 160, 81-88.
Dorn, et al. "Evaluation of a High-Throughput Fluorescence Assay Method for hERG Potassium Channel Inhibition", *J. Biomol. Screen*, 2005, 10, 339-347.

(Continued)

*Primary Examiner* — Matthew P Coughlin
(74) *Attorney, Agent, or Firm* — Cooley LLP; Ivor R. Elrifi; Chen Chen

(57) ABSTRACT

The present application provides a compound of formula I:

(I)

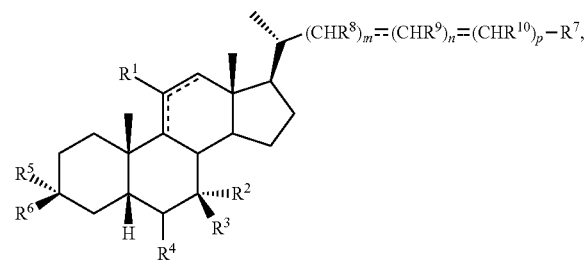

or a pharmaceutically acceptable salt, solvate, or amino acid conjugate thereof, wherein $R^1$-$R^{10}$, m, n, p, and === are as described herein. The present invention relates generally to FXR modulators and to methods of making and using said compounds.

10 Claims, No Drawings

(56) References Cited

OTHER PUBLICATIONS

GenBank Accession No. NM 021745.
GenBank Accession No. NM 009108.
GenBank Accession No. NM 005123.
Gioiello, et al., "Bile Acid Derivatives as Ligands of the Farnesoid X Receptor: Molecular Determinants for Bile Acid Binding and Receptor Modulation", Curr. Top. Med. Chem., 2014, 14, 2159-2174.
Heery, et al., "A signature motif in transcriptional co-activators mediates binding to nuclear receptors", Nature, 1997, 387, 733-736.
Huber, et al., "Generation of multiple farnesoid-X-receptor isoforms through the use of alternative promoters", Gene, 2002, 290, 35-43.
Kangas, et al., "Bioluminescence of Cellular ATP: A New Method for Evaluating Cytotoxic Agents in Vitro", Medical Biology, 1984, 62, 338-343.
Kawamata, et al., "A G Protein-coupled Receptor Responsive to Bile Acids", J. Biol. Chem., 2003, 278, 9435-9440.
Makishima, et al., "Identification of a Nuclear Receptor for Bile Acids", Science, 1999, 284, 1362-1365.
Maruyama, et al., "Identification of membrane-type receptor for bile acids (M-BAR)", Biochem. Biophys. Res. Commun., 2002, 298, 714-719.
Nolte, et al., "Ligand binding and co-activator assembly of the peroxisome proliferator-activated receptor-γ", Nature, 1998, 395, 137-143.
Obach, et al., "The Utility of in Vitro Cytochrome P450 Inhibition Data in the Prediction of Drug-Drug Interactions", J. Pharmacol. Exp. Ther., 2006, 316, 336-348.
Onate, et al., "Sequence and Characterization of a Coactivator for the Steroid Hormone Receptor Superfamily", Science, 1995, 270, 1354-1357.
Parks, et al., "Bile Acids: Natural Ligands for an Orphan Nuclear Receptor", Science, 1999, 284, 1365-1368.
Pellicciari, et al., "Discovery of 6α-Ethyl-23(S)-methylcholic Acid (S-EMCA, INT-777) as a Potent and Selective Agonist for the TGR5 Receptor, a Novel Target for Diabesity", J. Med. Chem., 2009, 52, 7958-7961.
Petty, et al., "Comparison of MTT and ATP-Based Assays for the Measurement of Viable Cell Number", J. Biolumin. Chemilumin., 1995, 10, 29-34.
Rizzo, et al., "Functional Characterization of the Semisynthetic Bile Acid Derivative INT-767, a Dual Farnesoid X Receptor and TGR5 Agonist", Mol. Pharm., 2010, 78, 617-630.
Storer, et al., "Revalidation of the in vitro alkaline elution/rat hepatocyte assay for DNA damage: improved criteria for assessment of cytotoxicity and genotoxicity and results for 81 compounds", Mutation Research, 1996, 368, 59-101.
Torchia, et al., "The transcriptional co-activator p/CIP binds CBP and mediates nuclear-receptor function", Nature, 1997, 387, 677-684.
Wang, et al., "SRC-1 and GRIP1 Coactivate Transcription with Hepatocyte Nuclear Factor 4", J. Biol. Chem., 1998, 273, 30847-30850.
Zhu, et al. "Cloning and Identification of Mouse Steroid Receptor Coactivator-1 (mSRC-1), as a Coactivator of Peroxisome Proliferator-Activated Receptor γ", Gene Expr., 1996, 6, 185-195.
PUBCHEM, Substance Record for SID 85207872, Sep. 28, 2009, 5 pages.
PUBCHEM, Substance Record for SID 236277322, Feb. 13, 2015, 7 pages.
Vandenheuvel, F. A. "Gas-liquid chromatographic studies of reactions and structural relationships of steroids: II. Positions 3, 11, and 20 in the pregnane series", Journal of Chromatography, 1975, vol. 103, p. 113-134.
D'Amore C. et al. "Design, Synthesis, and Biological Evaluation of Potent Dual Agonists of Nuclear and Membrane Bile Acid Receptors", Journal of Medicinal Chemistry, vol. 57, No. 3, 2014, pp. 937-954.
Festa C. et al. "Exploitation of Cholane Scaffold for the Discovery of Potent and Selective Farnesoid X Receptor (FXR) and G-Protein Coupled Bile Acid Receptor (GP-BAR1) Ligands", Journal of Medicial Chemistry, vol. 57, No. 20, 2014, pp. 8477-8495.
Ishida H. et al. "Study on the Bile Salts from Sunfish, Mola mola L. I. The Structures of Sodium Cyprinol Sulfates, the Sodium Salt of a New Bile Acid Conjugated with Taurine, and a New Bile Alcohol and Its New Sodium Sulfates", Chemical & Pharmaceutical Bulletin, vol. 46, No. 1, 1998, pp. 12-16.
Long W. et al. "Partial Synthesis of Compounds Related to Adrenal Cortical Hormones IX. Stepwise Degradation of the Side Chain of 3alpha,11alpha-Dihydroxycholanic Acid*", Journal of Biological Chemistry, vol. 165, No. 1,1946, pp. 197-209.
Pellicciari R. et al. "Discovery of 3[alpha],7[alpha],11[beta]-Trihydroxy-6[alpha]-ethyl-5[beta]-cholan-24-oic Acid (TC-100), a Novel Bile Acid as Potent and Highly Selective FXR Agonist for Enterohepatic Disorders", Journal of Medicinal Chemistry, vol. 59, No. 19, 2016, pp. 9201-9214.
Vidic H. J. et al. "Microbial transformations of steroids, XV. Microbial hydroxylation of 3.alpha.-acetoxy-5.beta.-pregnane-20-carboxylic acid and of its methyl ester by Calonectria decora and Syncephalastrum racemosum", Chemische Berichte, vol. 111, No. 6, 1978, pp. 2143-2151.
Borgstrom E., et al. "Partial synthesis of compounds related to adrenal cortical hormones: XI. Reactions of ring c ketols in the preparation of an 11-keto bile acid", The Journal of Biological Chemistry, 1949, vol. 177, pp. 951-967.
Cronholm T., et al. "Excretion of endogenous steroids and metabolites of [4-$^{14}$C]pregnenolone in bile of female rats", European Journal of Biochemistry, 1971, vol. 19, No. 3, pp. 424-432.

* cited by examiner

FARNESOID X RECEPTOR MODULATORS

BACKGROUND

Farnesoid X receptor (FXR) is a nuclear receptor that functions as a bile acid sensor controlling bile acid homeostasis. FXR is expressed in various organs and shown to be involved in many diseases and conditions, such as liver diseases, lung diseases, renal diseases, intestinal diseases, and heart diseases, and biological processes, including glucose metabolism, insulin metabolism, and lipid metabolism. A number of natural bile acids are FXR modulators, and are able to regulate FXR-mediated diseases and conditions (Gioiello, et al., 2014 Curr. Top. Med. Chem. 14, 2159). For example, natural bile acids such as chenodeoxycholic acid (CDCA), deoxycholic acid (DCA), lithocholic acid (LCA), and the taurine and glycine conjugates thereof serve as FXR ligands.

Derivatives of natural bile acids have also been described as FXR modulators. European Patent No. 0312867 describes 6-methyl derivatives of natural biliary acids such as ursodeoxycholic acid, ursocholic acid, chenodeoxycholic acid and cholic acid. WO 2002/75298 discloses 3α,7α-dihydroxy-6α-ethyl-5β-cholan-24-oic acid (hereinafter also referred to as 6-ethyl-chenodeoxycholic acid, or 6-ECDCA), salts, solvates, and amino acid conjugates thereof as FXR modulators, which can be used to prevent or treat FXR-mediated diseases or conditions.

However, it is well known that natural bile acids and bile acid derivatives modulate not only other nuclear hormone receptors, but are also modulators for the G protein-coupled receptor (GPCR) TGR5. Receptor selectivity is a problem in connection with the development of a therapeutic compound directed to modulating a nuclear hormone receptor such as FXR. A non-selective therapeutic compound may carry an increased risk of side effects. Other obstacles to overcome in the development of a therapeutic compound include a non-suitable pharmacokinetic profile, safety issues such as toxicity (e.g., liver) and undesirable drug-drug interactions.

Thus, there remains a need for additional selective FXR modulators suitable for drug development, for example, a compound that is selective against other nuclear receptors and/or does not significantly activate the bile acid GPCR TGR5.

SUMMARY

An objective of the present invention is to provide compounds that modulate FXR. In one aspect, the present invention provides a compound of formula I:

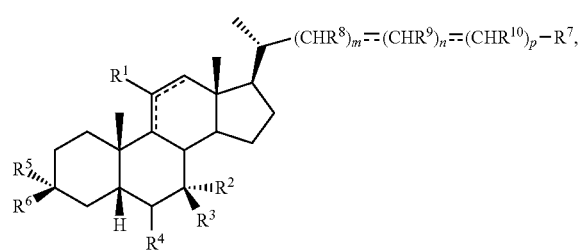

(I)

or a pharmaceutically acceptable salt, solvate, or amino acid conjugate thereof, wherein:

$R^1$ is OH, alkoxy, halogen, or oxo;

$R^2$ and $R^3$ are each independently H, OH, halogen, or alkyl optionally substituted with one or more halogen or OH, or $R^2$ and $R^3$ taken together with the carbon atom to which they are attached form a carbonyl;

$R^4$ is H, halogen, alkyl optionally substituted with one or more halogen or OH, alkenyl, or alkynyl;

$R^5$ and $R^6$ are each independently H, OH, $OSO_3H$, $OCOCH_3$, $OPO_3H_2$, or halogen, or $R^5$ and $R^6$ taken together with the carbon atom to which they are attached form a carbonyl;

$R^7$ is OH, $OSO_3H$, $SO_3H$, $OSO_2NH_2$, $SO_2NH_2$, $OPO_3H_2$, $PO_3H_2$, $CO_2H$, C(O)NHOH, tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, or 2,4-difluoro-3-hydroxyphenyl;

$R^8$, $R^9$, and $R^{10}$ are each independently H, OH, halogen, or alkyl optionally substituted with one or more halogen or OH, or $R^8$ and $R^9$ taken together with the carbon atoms to which they are attached form a 3- to 6-membered carbocyclic or heterocyclic ring comprising 1 or 2 heteroatoms selected from N, O, and S, or $R^9$ and $R^{10}$ taken together with the carbon atoms to which they are attached form a 3- to 6-membered carbocyclic or heterocyclic ring comprising 1 or 2 heteroatoms selected from N, O, and S;

m is 0, 1, or 2;

n is 0 or 1;

p is 0 or 1; and

═══ is a single or double bond, provided that when each ═══ is a single bond, the sum of m, n, and p is 2, $R^1$ is OH, and $R^8$, $R^9$, and $R^{10}$ are each H, then $R^7$ is not $CO_2H$.

The present invention further provides a pharmaceutical composition comprising a compound of formula I or a pharmaceutically acceptable salt, solvate, or amino acid conjugate thereof, and a pharmaceutically acceptable carrier or excipient.

The present invention also provides a method for treating or preventing a disease or condition mediated by FXR, comprising administering to a subject in need thereof an effective amount of a compound of formula I or a pharmaceutically acceptable salt, solvate, or amino acid conjugate thereof.

The present invention also provides for the manufacture of a medicament for treating or preventing a disease or condition mediated by FXR, wherein the medicament comprises a compound of formula I or a pharmaceutically acceptable salt, solvate, or amino acid conjugate thereof.

The present invention further provides compositions, including pharmaceutical compositions, for use in treating or preventing a disease or condition mediated by FXR, wherein the composition comprises a compound of formula I or a pharmaceutically acceptable salt, solvate, or amino acid conjugate thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. The materials, methods, and examples are illustrative only and are not intended to be limiting.

Other features and advantages of the invention will be apparent from the following detailed description.

DETAILED DESCRIPTION

Definitions

Certain terms used in the specification and claims are collected here.

As used herein, the phrase "a compound of the invention" refers to a compound of any one of formula I, II, III, IV, V, VI, VII, Ia, Ib, Ic, Id, Ie, Id, or any compound explicitly disclosed herein.

As used herein, the term "alkyl" refers to a straight-chain or branched saturated hydrocarbon moiety. The term "$C_1$-$C_6$ alkyl" refers to a straight-chain or branched hydrocarbon moiety having 1, 2, 3, 4, 5, or 6 carbon atoms. "$C_1$-$C_4$ alkyl" refers to a straight-chain or branched hydrocarbon moiety having 1, 2, 3, or 4 carbon atoms, including methyl, ethyl, n-propyl, isopropyl, n-butyl, isobutyl, sec-butyl, and t-butyl.

The term "alkenyl" refers to a straight-chain or branched hydrocarbon moiety containing at least one carbon-carbon double bond. Both the trans and cis isomers of the carbon-carbon double bond are encompassed under the term "alkenyl". Examples of alkenyl moieties include, but are not limited to, vinyl, allyl, 1-butenyl, 2-butenyl, 3-butenyl, and 2-hexenyl.

As used herein, "alkynyl" refers to a straight-chain or branched hydrocarbon moiety containing at least one carbon-carbon triple bond. Examples of alkynyl moieties include, but are not limited to, ethynyl, 2-propynyl, 5-but-1-en-3-ynyl, and 3-hexynyl.

The term "alkoxy" refers to a straight-chain or branched saturated hydrocarbon covalently attached to an oxygen atom. Examples of alkoxy moieties include, but are not limited to, methoxy, ethoxy, isopropyloxy, n-propoxy, n-butoxy, t-butoxy, and pentoxy.

As used herein, the term "halogen" refers to fluorine, bromine, chlorine and iodine.

The term "optionally substituted" refers to the indicated moiety which may or may not be substituted, and when substituted is mono-, di-, or tri-substituted, such as with 1, 2, or 3 substituents. In some instances, the substituent is halogen or OH.

As used herein, "carbocycle", "carbocyclic" or "carbocyclic ring" is intended to include any stable monocyclic or bicyclic ring having the specified number of carbons, any of which may be saturated, unsaturated, or aromatic. Carbocyclic ring includes cycloalkyl and aryl. For example, a $C_3$-$C_8$ carbocyclic ring is intended to include a monocyclic or bicyclic ring having 3, 4, 5, 6, 7, or 8 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, and phenyl.

As used herein, "heterocycle", "heterocyclic" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran. Examples of heterocyclic groups include, but are not limited to, benzimidazolyl, benzofuranyl, benzothiofuranyl, tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isoindazolyl, isoindolinyl, isoindolyl, isoquinolinyl, isothiazolyl, isoxazolyl, methylenedioxyphenyl, morpholinyl, pyridinyl, pyridyl, and pyrimidinyl.

As used herein, the term "cycloalkyl" refers to a saturated or unsaturated nonaromatic hydrocarbon mono- or multi-ring (e.g., fused, bridged, or spiro rings) system having 3 to 10 carbon atoms (e.g., $C_3$-$C_6$). Examples of cycloalkyl include, but are not limited to, cyclopropyl, cyclobutyl, cyclopentyl, cyclohexyl, cycloheptyl, cyclooctyl, cyclopentenyl, cyclohexenyl, and cycloheptenyl.

The term "heterocycloalkyl" refers to a saturated or unsaturated nonaromatic 3-8 membered monocyclic or bicyclic (fused, bridged, or spiro rings) having one or more heteroatoms (such as O, N, or S), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, and tetrahydrothiopyranyl and the like.

As used herein, any recited moiety which includes, but is not limited to, alkyl, alkenyl, alkynyl, alkoxy, carbocyclic ring, heterocyclic ring, cycloalkyl, heterocycloalkyl, etc. can be optionally substituted.

The term "FXR modulator" refers to any compound that interacts with the FXR receptor. The interaction is not limited to a compound acting as an antagonist, agonist, partial agonist, or inverse agonist of the FXR receptor. In one embodiment, the compound of the invention acts as an antagonist of the FXR receptor. In another aspect, the compound of the invention acts as an agonist of the FXR receptor. In another aspect, the compound of the invention acts as a partial agonist of the FXR receptor. In another aspect, the compound of the invention acts as an inverse agonist of the FXR receptor.

"Solvate", as used herein, refers to a solvent addition form of a compound of the invention that contains either stoichiometric or non-stoichiometric amounts of solvent. Some compounds have a tendency to trap a fixed molar ratio of solvent molecules in the crystalline solid state, thus forming a solvate. If the solvent is water, the solvate formed is a hydrate, and when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "amino acid conjugates" refers to conjugates of a compound of the invention with any suitable amino acid. Taurine (—$NH(CH_2)_2SO_3H$), glycine (—$NHCH_2CO_2H$), and sarcosine (—$N(CH_3)CH_2CO_2H$) are examples of amino acid conjugates. Suitable amino acid conjugates of the compounds have the added advantage of enhanced integrity in bile or intestinal fluids. Suitable amino acids are not limited to taurine, glycine, and sarcosine.

As defined herein, the term "metabolite" refers to glucuronidated and sulphated derivatives of the compounds described herein, wherein one or more glucuronic acid or sulphate moieties are linked to compound of the invention. Glucuronic acid moieties may be linked to the compounds through glycosidic bonds with the hydroxyl groups of the compounds (e.g., 3-hydroxyl, 7-hydroxyl, 11-hydroxyl, and/or the hydroxyl of the $R^7$ group). Sulphated derivatives of the compounds may be formed through sulphation of the hydroxyl groups (e.g., 3-hydroxyl, 7-hydroxyl, 11-hydroxyl, and/or the hydroxyl of the $R^7$ group). Examples of metabolites include, but are not limited to, 3-O-glucuronide, 7-O-glucuronide, 11-O-glucuronide, 3-O-7-O-diglucuronide, 3-O-11-O-triglucuronide, 7-O-11-O-triglucuronide, and 3-O-7-O-11-O-triglucuronide, of the compounds described herein, and 3-sulphate, 7-sulphate, 11-sulphate, 3,7-bisulphate, 3,11-bisulphate, 7,11-bisulphate, and 3,7,11-trisulphate, of the compounds described herein.

As used herein, "pharmaceutically acceptable salts" refer to derivatives of a compound of the invention wherein the parent compound is modified by forming acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulphamic, sulphanilic, sulphuric, tannic, tartaric, and toluene sulphonic.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier is "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A "composition" or "pharmaceutical composition" is a formulation containing a compound of the invention or a salt, solvate, or amino acid conjugate thereof In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the invention or salts thereof) in a unit dose of composition is an effective amount and is varied according to the particular treatment involved. One skilled in the art will appreciate that it may be necessary to make routine variations to the dosage depending on the age and condition of the patient. The dosage will also depend on the route of administration. A variety of routes are contemplated, including oral, ocular, ophthalmic, pulmonary, rectal, parenteral, transdermal, subcutaneous, intravenous, intramuscular, intraperitoneal, intranasal, and the like. Dosage forms for the topical or transdermal administration of a compound of this application include powders, sprays, ointments, pastes, creams, lotions, gels, solutions, patches and inhalants. In another embodiment, the active compound is mixed under sterile conditions with a pharmaceutically acceptable carrier, and with any preservatives, buffers, or propellants that are required.

The term "treating", as used herein, refers to relieving, lessening, reducing, eliminating, modulating, or ameliorating, i.e., causing regression of the disease state or condition.

The term "preventing", as used herein, refers to completely or almost completely stop a disease state or condition, from occurring in a patient or subject, especially when the patient or subject is predisposed to such or at risk of contracting a disease state or condition. Preventing can also include inhibiting, i.e., arresting the development, of a disease state or condition, and relieving or ameliorating, i.e., causing regression of the disease state or condition, for example when the disease state or condition may already be present.

The phrase "reducing the risk of", as used herein, refers to lowering the likelihood or probability of a central nervous system disease, inflammatory disease and/or metabolic disease from occurring in a patient, especially when the subject is predisposed to such occurrence.

"Combination therapy" (or "co-therapy") refers to the administration of a compound of the invention and at least a second agent as part of a specific treatment regimen intended to provide the beneficial effect from the co-action of these therapeutic agents (i.e., the compound of the invention and at least a second agent). The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present application. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or mechanical treatments). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

An "effective amount" of a compound of the invention, or a combination of compounds is an amount (quantity or concentration) of compound or compounds. In one embodiment, when a therapeutically effective amount of a compound is administered to a subject in need of treatment symptoms arising from the disease are ameliorated immediately or after administration of the compound one or more times. The amount of the compound to be administered to a subject will depend on the particular disorder, the mode of administration, co-administered compounds, if any, and the characteristics of the subject, such as general health, other diseases, age, sex, genotype, body weight, and tolerance to drugs. The skilled artisan will be able to determine appropriate dosages depending on these and other factors.

The term "prophylactically effective amount" means an amount (quantity or concentration) of a compound of the present invention, or a combination of compounds, that is administered to prevent or reduce the risk of a disease—in other words, an amount needed to provide a preventative or prophylactic effect. The amount of the present compound to be administered to a subject will depend on the particular disorder, the mode of administration, co-administered compounds, if any, and the characteristics of the subject, such as general health, other diseases, age, sex, genotype, body weight, and tolerance to drugs. The skilled artisan will be able to determine appropriate dosages depending on these and other factors. A "subject" includes mammals, e.g., humans, companion animals (e.g., dogs, cats, birds, and the like), farm animals (e.g., cows, sheep, pigs, horses, and the like), and laboratory animals (e.g., rats, mice, guinea pigs, and the like). Typically, the subject is human.

As used herein, farnesoid X receptor or FXR refers to all mammalian forms of such receptor including, for example, alternative splice isoforms and naturally occurring isoforms (see, e.g., Huber et al., Gene 290:35-43 (2002)). Representative FXR species include, without limitation rat FXR (GenBank Accession No. NM 021745), mouse FXR (GenBank Accession No. NM 009108), and human FXR (GenBank Accession No. NM 005123).

Compounds of the Invention

In one aspect, the present disclosure provides a compound of formula I:

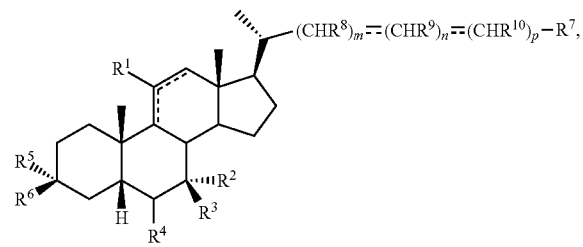

(I)

or a pharmaceutically acceptable salt, solvate, or amino acid conjugate thereof, wherein:

$R^1$ is OH, alkoxy, halogen, or oxo;

$R^2$ and $R^3$ are each independently H, OH, halogen, or alkyl optionally substituted with one or more halogen or OH, or $R^2$ and $R^3$ taken together with the carbon atom to which they are attached form a carbonyl;

$R^4$ is H, halogen, alkyl optionally substituted with one or more halogen or OH, alkenyl, or alkynyl;

$R^5$ and $R^6$ are each independently H, OH, $OSO_3H$, $OCOCH_3$, $OPO_3H_2$, or halogen, or $R^5$ and $R^6$ taken together with the carbon atom to which they are attached form a carbonyl;

$R^7$ is OH, $OSO_3H$, $SO_3H$, $OSO_2NH_2$, $SO_2NH_2$, $OPO_3H_2$, $PO_3H_2$, $CO_2H$, $C(O)NHOH$, tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, or 2,4-difluoro-3-hydroxyphenyl;

$R^8$, $R^9$, and $R^{10}$ are each independently H, OH, halogen, or alkyl optionally substituted with one or more halogen or OH, or $R^8$ and $R^9$ taken together with the carbon atoms to which they are attached form a 3- to 6-membered carbocyclic or heterocyclic ring comprising 1 or 2 heteroatoms selected from N, O, and S, or $R^9$ and $R^{10}$ taken together with the carbon atoms to which they are attached form a 3- to 6-membered carbocyclic or heterocyclic ring comprising 1 or 2 heteroatoms selected from N, O, and S;

m is 0, 1, or 2;

n is 0 or 1;

p is 0 or 1; and

═ is a single or double bond, provided that when each ═ is a single bond, the sum of m, n, and p is 2, $R^1$ is OH, and $R^8$, $R^9$, and $R^{10}$ are each H, then $R^7$ is not $CO_2H$.

In one of the embodiments, the present disclosure provides a compound of formula Ia:

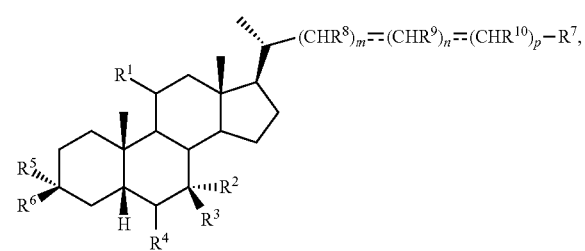

(Ia)

or a pharmaceutically acceptable salt, solvate, or amino acid conjugate thereof.

In one of the embodiments, the present disclosure provides a compound of formula Ib or Ic:

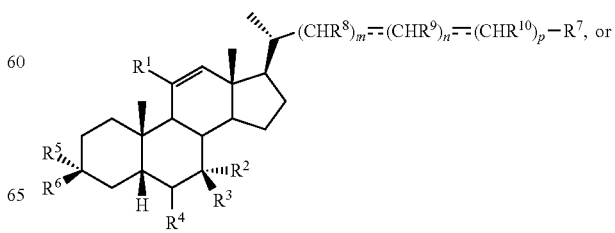

(Ib)

-continued (Ic)

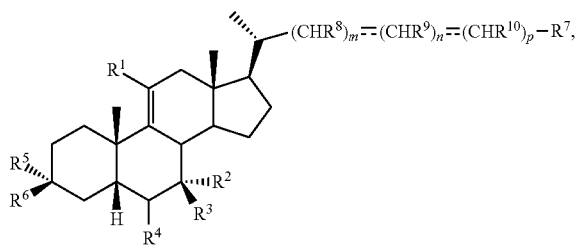

(Ie)

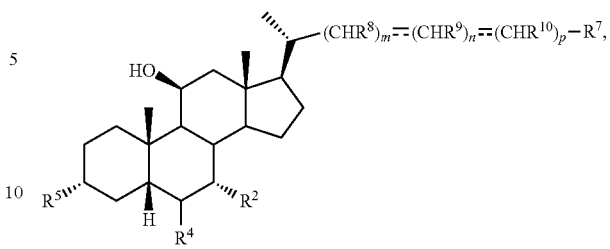

or a pharmaceutically acceptable salt, solvate, or amino acid conjugate thereof.

In one of the embodiments, the present disclosure provides compounds of formula I and Ia-Ic, wherein $R^1$ is OH, alkoxy, or oxo.

In one of the embodiments, the present disclosure provides compounds of formula I and Ia-Ic, wherein $R^1$ is OH or alkoxy.

In one of the embodiments, the present disclosure provides compounds of formula I and Ia-Ic, wherein $R^1$ is halogen.

In one of the embodiments, the present disclosure provides compounds of formula I and Ia-Ic, wherein $R^1$ is OH.

In one of the embodiments, the present disclosure provides compounds of formula I and Ia-Ic, wherein $R^1$ is alkoxy.

In one of the embodiments, the present disclosure provides compounds of formula I and Ia-Ic, wherein $R^3$ is H.

In one of the embodiments, the present disclosure provides compounds of formula I and Ia-Ic, wherein $R^3$ is OH or halogen.

In one of the embodiments, the present disclosure provides compounds of formula I and Ia-Ic, wherein $R^3$ is $C_1$-$C_6$ alkyl optionally substituted with one or more halogen or OH.

In one of the embodiments, the present disclosure provides compounds of formula I and Ia-Ic, wherein $R^6$ is OH or H.

In one of the embodiments, the present disclosure provides compounds of formula I and Ia-Ic, wherein $R^6$ is $OSO_3H$, $OCOCH_3$, or $OPO_3H_2$.

In one of the embodiments, the present disclosure a compound of formula Id:

(Id)

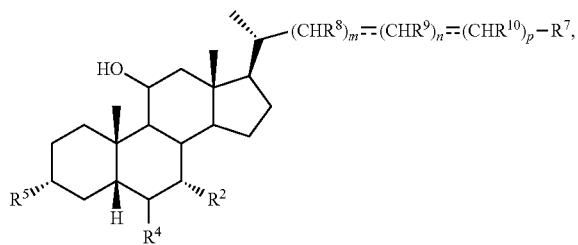

or a pharmaceutically acceptable salt, solvate, or amino acid conjugate thereof.

In one of the embodiments, the present disclosure a compound is of formula Ie:

or a pharmaceutically acceptable salt, solvate, or amino acid conjugate thereof.

In one of the embodiments, the present disclosure provides compounds of formula I and Ia-Id, wherein $R^7$ is OH, $OSO_3H$, $SO_3H$, $OSO_2NH_2$, $SO_2NH_2$, $OPO_3H_2$, $PO_3H_2$, $CO_2H$, or C(O)NHOH.

In one of the embodiments, the present disclosure provides compounds of formula I and Ia-Id, wherein $R^7$ is OH, $OSO_3H$, $OSO_2NH_2$, $OPO_3H_2$, or $CO_2H$.

In one of the embodiments, the present disclosure provides compounds of formula I and Ia-Id, wherein $R^7$ is OH.

In one of the embodiments, the present disclosure provides compounds of formula I and Ia-Id, wherein $R^7$ is $CO_2H$.

In one of the embodiments, the present disclosure provides compounds of formula I and Ia-Id, wherein $R^7$ is $OSO_3H$.

In one of the embodiments, the present disclosure provides compounds of formula I and Ia-Id, wherein $R^7$ is $SO_3H$.

In one of the embodiments, the present disclosure provides compounds of formula I and Ia-Id, wherein $R^7$ is $OSO_2NH_2$ or $SO_2NH_2$.

In one of the embodiments, the present disclosure provides compounds of formula I and Ia-Id, wherein $R^7$ is $OPO_3H_2$, $PO_3H_2$, or C(O)NHOH.

In one of the embodiments, the present disclosure provides compounds of formula I and Ia-Id, wherein $R^7$ is tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, or 2,4-difluoro-3-hydroxyphenyl.

In one of the embodiments, the present disclosure provides compounds of formula I and Ia-Id, wherein $R^7$ is OH, $OSO_3H$, $OSO_2NH_2$, $OPO_3H_2$, $CO_2H$, tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, or 2,4-difluoro-3-hydroxyphenyl.

In one of the embodiments, the present disclosure provides compounds of formula I and Ia-Id, wherein $R^2$ is OH.

In one of the embodiments, the present disclosure provides compounds of formula I and Ia-Id, wherein $R^2$ is H or halogen.

In one of the embodiments, the present disclosure provides compounds of formula I and Ia-Id, wherein $R^2$ is $C_1$-$C_6$ alkyl optionally substituted with one or more halogen or OH.

In one of the embodiments, the present disclosure provides compounds of formula I and Ia-Id, wherein $R^5$ is OH or H.

In one of the embodiments, the present disclosure provides compounds of formula I and Ia-Id, wherein $R^5$ is $OSO_3H$, $OCOCH_3$, or $OPO_3H_2$.

In one of the embodiments, the present disclosure provides compounds of formula I and Ia-Id, wherein $R^5$ and $R^6$ taken together with the carbon atom to which they are attached form a carbonyl.

In one of the embodiments, the present disclosure provides compounds of formula I and Ia-Id, wherein $R^4$ is H or halogen.

In one of the embodiments, the present disclosure provides compounds of formula I and Ia-Id, wherein $R^4$ is $C_1$-$C_6$ alkyl optionally substituted with one or more halogen or OH.

In one of the embodiments, the present disclosure provides compounds of formula I and Ia-Id, wherein $R^4$ is $C_2$-$C_6$ alkenyl or $C_2$-$C_6$ alkynyl.

In one of the embodiments, the present disclosure provides compounds of formula I and Ia-Id, wherein $R^4$ is methyl, ethyl, or propyl.

In one of the embodiments, the present disclosure provides compounds of formula I and Ia-Id, wherein m is 0.

In one of the embodiments, the present disclosure provides compounds of formula I and Ia-Id, wherein m is 1.

In one of the embodiments, the present disclosure provides compounds of formula I and Ia-Id, wherein m is 2.

In one of the embodiments, the present disclosure provides compounds of formula I and Ia-Id, wherein n is 1.

In one of the embodiments, the present disclosure provides compounds of formula I and Ia-Id, wherein p is 0.

In one of the embodiments, the present disclosure provides compounds of formula I and Ia-Id, wherein $R^4$ is in the α-position.

In one of the embodiments, the present disclosure provides compounds of formula I and Ia-Id, wherein $R^1$ is in the β-position.

In one of the embodiments, the present disclosure provides compounds of formula I, wherein the compound is selected from:

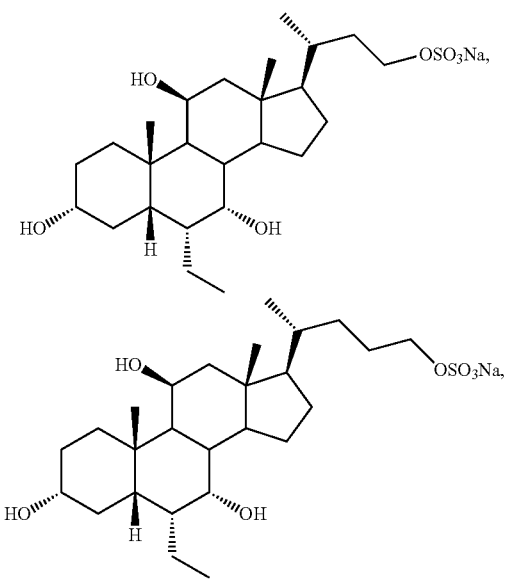

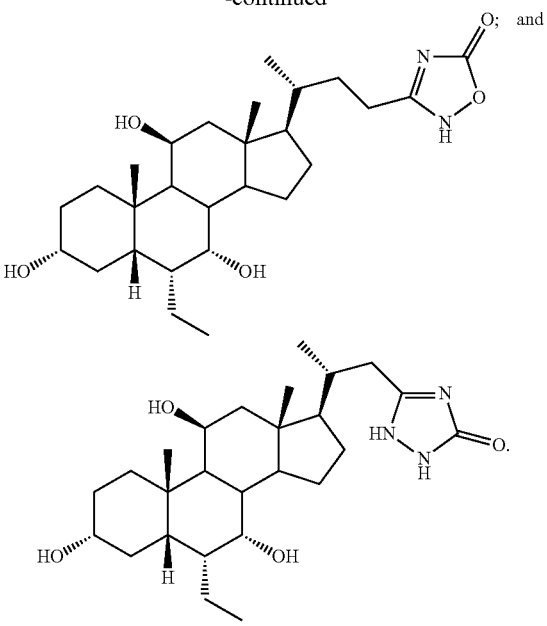

In one of the embodiments, the present disclosure provides salts of compounds of formula I and Ia-Id.

In one of the embodiments, the present disclosure provides compounds of formula I and Ia-Id, wherein $R^7$ is $OSO_3^-$.

In one of the embodiments, the present disclosure provides compounds of formula I and Ia-Id, wherein $R^7$ is $OSO_3^-Na^+$.

In one of the embodiments, the present disclosure provides a compound of formula I

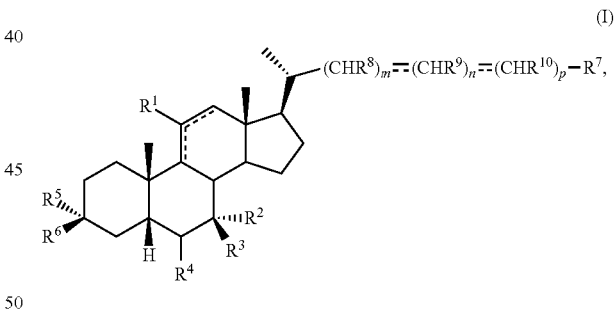

or a pharmaceutically acceptable salt, solvate, or amino acid conjugate thereof, wherein:

$R^1$ is alkoxy or oxo;

$R^2$ and $R^3$ are each independently H, OH, halogen, or alkyl optionally substituted with one or more halogen or OH, or $R^2$ and $R^3$ taken together with the carbon atom to which they are attached form a carbonyl;

$R^4$ is H, halogen, alkyl optionally substituted with one or more halogen or OH, alkenyl, or alkynyl;

$R^5$ and $R^6$ are each independently H, OH, $OSO_3H$, $OCOCH_3$, $OPO_3H_2$, or halogen, or $R^5$ and $R^6$ taken together with the carbon atom to which they are attached form a carbonyl;

$R^7$ is OH, $OSO_3H$, $SO_3H$, $OSO_2NH_2$, $SO_2NH_2$, $OPO_3H_2$, $PO_3H_2$, $CO_2H$, $C(O)NHOH$, tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, or 2,4-difluoro-3-hydroxyphenyl;

$R^8$, $R^9$, and $R^{10}$ are each independently H, OH, halogen, or alkyl optionally substituted with one or more halogen or OH, or $R^8$ and $R^9$ taken together with the carbon atoms to which they are attached form a 3- to 6-membered carbocyclic or heterocyclic ring comprising 1 or 2 heteroatoms selected from N, O, and S, or $R^9$ and $R^{10}$ taken together with the carbon atoms to which they are attached form a 3- to 6-membered carbocyclic or heterocyclic ring comprising 1 or 2 heteroatoms selected from N, O, and S;

m is 0, 1, or 2;

n is 0 or 1;

p is 0 or 1; and

═ is a single or double bond.

In one of the embodiments, the present disclosure provides a compound of formula I:

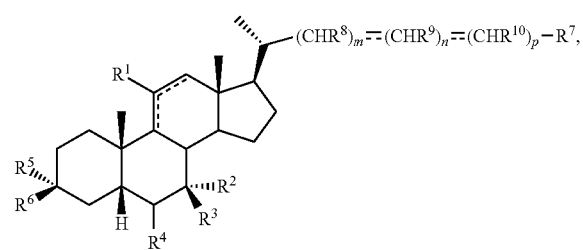

(I)

or a pharmaceutically acceptable salt, solvate, or amino acid conjugate thereof, wherein:

$R^1$ is OH, alkoxy, halogen, or oxo;

$R^2$ and $R^3$ are each independently H, OH, halogen, or alkyl optionally substituted with one or more halogen or OH, or $R^2$ and $R^3$ taken together with the carbon atom to which they are attached form a carbonyl;

$R^4$ is H, halogen, alkyl optionally substituted with one or more halogen or OH, alkenyl, or alkynyl;

$R^5$ and $R^6$ are each independently H, OH, $OSO_3H$, $OCOCH_3$, $OPO_3H_2$, or halogen, or $R^5$ and $R^6$ taken together with the carbon atom to which they are attached form a carbonyl;

$R^7$ is $OSO_3H$, $OSO_2NH_2$, $OPO_3H_2$, C(O)NHOH, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, or 2,4-difluoro-3-hydroxyphenyl;

$R^8$, $R^9$, and $R^{10}$ are each independently H, OH, halogen, or alkyl optionally substituted with one or more halogen or OH, or $R^8$ and $R^9$ taken together with the carbon atoms to which they are attached form a 3- to 6-membered carbocyclic or heterocyclic ring comprising 1 or 2 heteroatoms selected from N, O, and S, or $R^9$ and $R^{10}$ taken together with the carbon atoms to which they are attached form a 3- to 6-membered carbocyclic or heterocyclic ring comprising 1 or 2 heteroatoms selected from N, O, and S;

m is 0, 1, or 2;

n is 0 or 1;

p is 0 or 1; and

═ is a single or double bond.

In one of the embodiments, the present disclosure provides a compound of formula I:

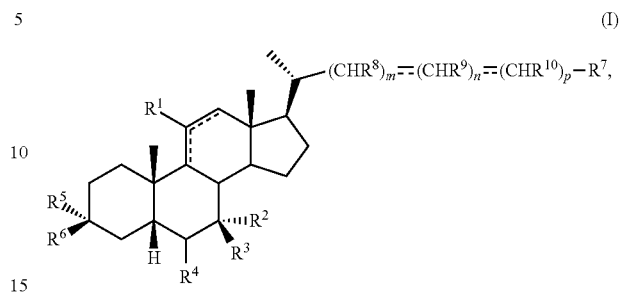

(I)

or a pharmaceutically acceptable salt, solvate, or amino acid conjugate thereof, wherein:

$R^1$ is OH, alkoxy, halogen, or oxo;

$R^2$ is H, OH, halogen, or alkyl optionally substituted with one or more halogen or OH, or $R^2$ and $R^3$ taken together with the carbon atom to which they are attached form a carbonyl;

$R^3$ is OH, halogen, or alkyl optionally substituted with one or more halogen or OH, or $R^2$ and $R^3$ taken together with the carbon atom to which they are attached form a carbonyl;

$R^4$ is H, halogen, alkyl optionally substituted with one or more halogen or OH, alkenyl, or alkynyl;

$R^5$ and $R^6$ are each independently H, OH, $OSO_3H$, $OCOCH_3$, $OPO_3H_2$, or halogen, or $R^5$ and $R^6$ taken together with the carbon atom to which they are attached form a carbonyl;

$R^7$ is OH, $OSO_3H$, $SO_3H$, $OSO_2NH_2$, $SO_2NH_2$, $OPO_3H_2$, $PO_3H_2$, $CO_2H$, C(O)NHOH, tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, or 2,4-difluoro-3-hydroxyphenyl;

$R^8$, $R^9$, and $R^{10}$ are each independently H, OH, halogen, or alkyl optionally substituted with one or more halogen or OH, or $R^8$ and $R^9$ taken together with the carbon atoms to which they are attached form a 3- to 6-membered carbocyclic or heterocyclic ring comprising 1 or 2 heteroatoms selected from N, O, and S, or $R^9$ and $R^{10}$ taken together with the carbon atoms to which they are attached form a 3- to 6-membered carbocyclic or heterocyclic ring comprising 1 or 2 heteroatoms selected from N, O, and S;

m is 0, 1, or 2;

n is 0 or 1;

p is 0 or 1; and

═ is a single or double bond.

In one of the embodiments, the present disclosure a compound of formula I:

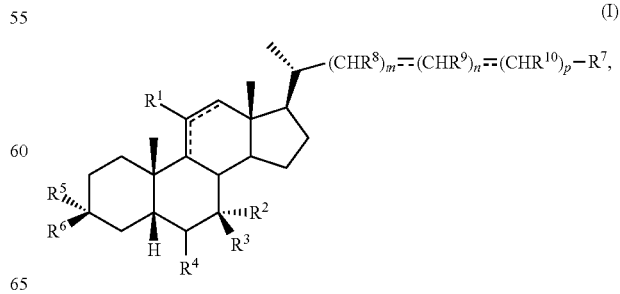

(I)

or a pharmaceutically acceptable salt, solvate, or amino acid conjugate thereof, wherein:

$R^1$ is OH, alkoxy, halogen, or oxo;

$R^2$ and $R^3$ are each independently H, OH, halogen, or alkyl optionally substituted with one or more halogen or OH, or $R^2$ and $R^3$ taken together with the carbon atom to which they are attached form a carbonyl;

$R^4$ is H, halogen, alkyl optionally substituted with one or more halogen or OH, alkenyl, or alkynyl;

$R^5$ is OH, $OSO_3H$, $OCOCH_3$, $OPO_3H_2$, or halogen;

$R^6$ is H, OH, $OSO_3H$, $OCOCH_3$, $OPO_3H_2$, or halogen, or $R^5$ and $R^6$ taken together with the carbon atom to which they are attached form a carbonyl;

$R^7$ is OH, $OSO_3H$, $SO_3H$, $OSO_2NH_2$, $SO_2NH_2$, $OPO_3H_2$, $PO_3H_2$, $CO_2H$, C(O)NHOH, tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, or 2,4-difluoro-3-hydroxyphenyl;

$R^8$, $R^9$, and $R^{10}$ are each independently H, OH, halogen, or alkyl optionally substituted with one or more halogen or OH, or $R^8$ and $R^9$ taken together with the carbon atoms to which they are attached form a 3- to 6-membered carbocyclic or heterocyclic ring comprising 1 or 2 heteroatoms selected from N, O, and S, or $R^9$ and $R^{10}$ taken together with the carbon atoms to which they are attached form a 3- to 6-membered carbocyclic or heterocyclic ring comprising 1 or 2 heteroatoms selected from N, O, and S;

m is 0, 1, or 2;

n is 0 or 1;

p is 0 or 1; and

═ is a single or double bond.

In one of the embodiments, the present disclosure provides a compound of formula I:

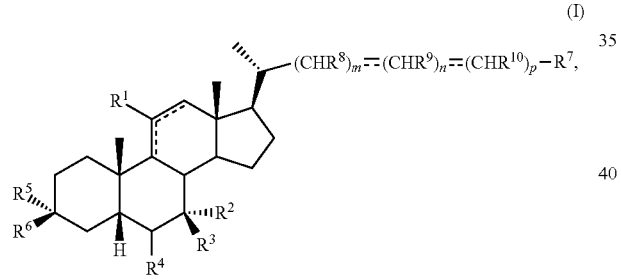

(I)

or a pharmaceutically acceptable salt, solvate, or amino acid conjugate thereof, wherein:

$R^1$ is OH, alkoxy, halogen, or oxo;

$R^2$ and $R^3$ are each independently H, OH, halogen, or alkyl optionally substituted with one or more halogen or OH, or $R^2$ and $R^3$ taken together with the carbon atom to which they are attached form a carbonyl;

$R^4$ is H, halogen, alkyl optionally substituted with one or more halogen or OH, alkenyl, or alkynyl;

$R^5$ is H, OH, $OSO_3H$, $OCOCH_3$, $OPO_3H_2$, or halogen;

$R^6$ is OH, $OSO_3H$, $OCOCH_3$, $OPO_3H_2$, or halogen, or $R^5$ and $R^6$ taken together with the carbon atom to which they are attached form a carbonyl;

$R^7$ is OH, $OSO_3H$, $SO_3H$, $OSO_2NH_2$, $SO_2NH_2$, $OPO_3H_2$, $PO_3H_2$, $CO_2H$, C(O)NHOH, tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, or 2,4-difluoro-3-hydroxyphenyl;

$R^8$, $R^9$, and $R^{10}$ are each independently H, OH, halogen, or alkyl optionally substituted with one or more halogen or OH, or $R^8$ and $R^9$ taken together with the carbon atoms to which they are attached form a 3- to 6-membered carbocyclic or heterocyclic ring comprising 1 or 2 heteroatoms selected from N, O, and S, or $R^9$ and $R^{10}$ taken together with the carbon atoms to which they are attached form a 3- to 6-membered carbocyclic or heterocyclic ring comprising 1 or 2 heteroatoms selected from N, O, and S;

m is 0, 1, or 2;

n is 0 or 1;

p is 0 or 1; and

═ is a single or double bond.

In one of the embodiments, the present disclosure provides a compound of formula I, wherein $R_7$ is OH.

In one of the embodiments, the present disclosure provides a compound of formula I, wherein the compound is selected from:

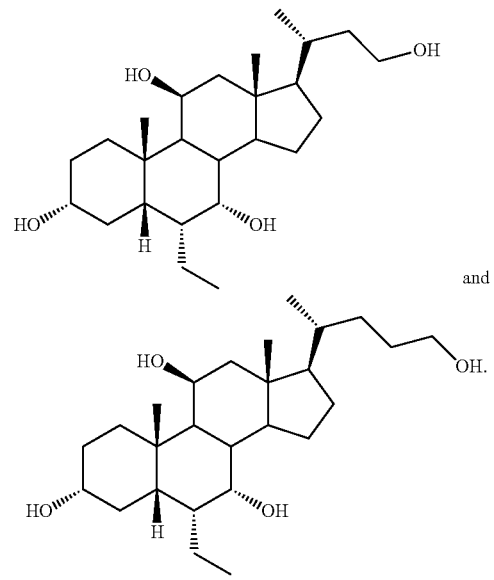 [SMILES: CC[C@H]1[C@@H](O)C2C3CC[C@H]([C@H](C)CCO)[C@@]3(C)C[C@H](O)C2[C@@]2(C)CC[C@@H](O)C[C@@H]12 ; CC[C@H]1[C@@H](O)C2C3CC[C@H]([C@H](C)CCCO)[C@@]3(C)C[C@H](O)C2[C@@]2(C)CC[C@@H](O)C[C@@H]12]

and

In one embodiment, the compound is of formula II:

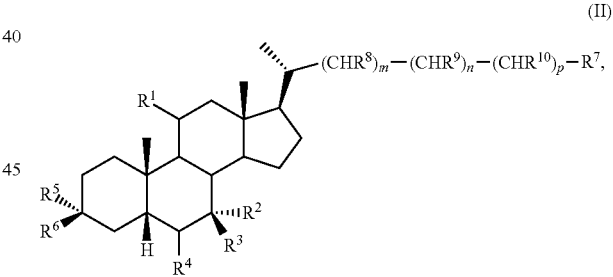

(II)

or a pharmaceutically acceptable salt, solvate, or amino acid conjugate thereof.

In another embodiment, the compound is of formula III:

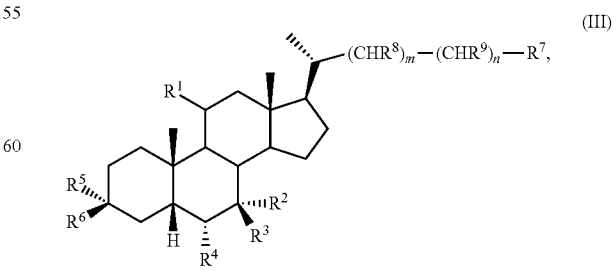

(III)

or a pharmaceutically acceptable salt, solvate, or amino acid conjugate thereof.

In yet another embodiment, the compound is of formula IV:

(IV)

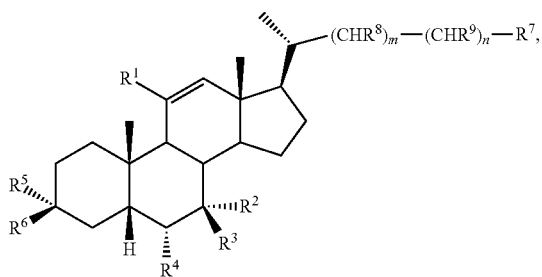

or a pharmaceutically acceptable salt, solvate, or amino acid conjugate thereof.

In one embodiment, the compound is of formula V:

(V)

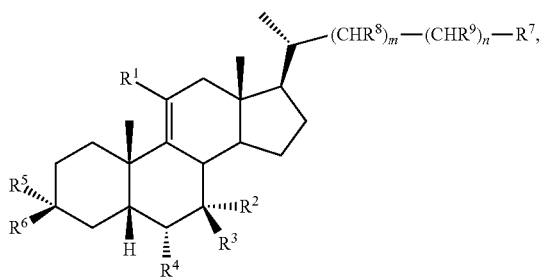

or a pharmaceutically acceptable salt, solvate, or amino acid conjugate thereof.

In another embodiment, the compound is of formula VI:

(VI)

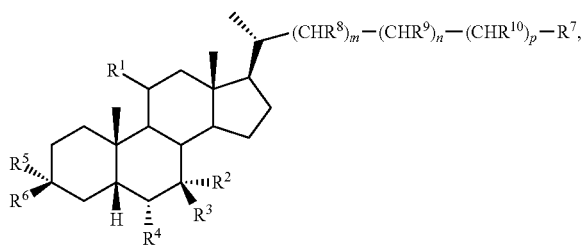

or a pharmaceutically acceptable salt, solvate, or amino acid conjugate thereof.

In another embodiment, the compound is of formula VII:

(VII)

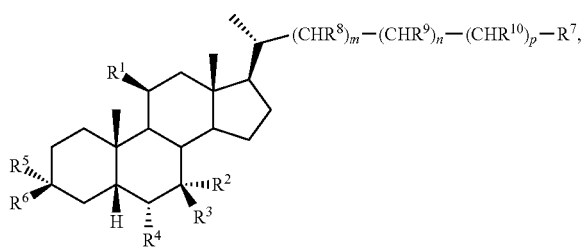

or a pharmaceutically acceptable salt, solvate, or amino acid conjugate thereof.

In one embodiment, the present disclosure relates to a compound of formula I, II, III, IV, V, VI, or VII, wherein $R^1$ is OH. In another embodiment, the present disclosure relates to a compound of formula I, II, III, IV, V, VI, or VII, wherein $R^1$ is halogen. In another embodiment, $R^1$ is fluoro. In another embodiment, the present disclosure relates to a compound of formula I, II, III, IV, V, VI, or VII, wherein $R^1$ is $C_1$-$C_6$ alkoxy. In one embodiment, the present disclosure relates to a compound of formula I, II, or III, wherein $R^1$ is oxo.

In another embodiment, the present disclosure relates to a compound of formula I, II, III, IV, V, VI, or VII, wherein $R^2$ is OH. In one embodiment, the present disclosure relates to a compound of formula I, II, III, IV, V, VI, or VII, wherein $R^2$ is H or halogen. In another embodiment, the present disclosure relates to a compound of formula I, II, III, IV, V, VI, or VII, wherein $R^2$ is $C_1$-$C_6$ alkyl optionally substituted with one or more halogen or OH.

In one embodiment, the present disclosure relates to a compound of formula I, II, III, IV, V, VI, or VII, wherein $R^1$ is OH and $R^2$ is OH.

In one embodiment, the present disclosure relates to a compound of formula I, II, III, IV, V, VI, or VII, wherein $R^1$ is OH and $R^2$ is H or halogen.

In one embodiment, the present disclosure relates to a compound of formula I, II, III, IV, V, VI, or VII, wherein $R^1$ is OH and $R^2$ is $C_1$-$C_6$ alkyl optionally substituted with one or more halogen or OH.

In one embodiment, the present disclosure relates to a compound of formula I, II, III, IV, V, VI, or VII, wherein $R^3$ is H. In one embodiment, the present disclosure relates to a compound of formula I, II, III, IV, V, VI, or VII wherein $R^3$ is OH or halogen. In another embodiment, the present disclosure relates to a compound of formula I, II, III, IV, V, VI, or VII, wherein $R^3$ is $C_1$-$C_6$ alkyl optionally substituted with one or more halogen or OH.

In one embodiment, the present disclosure relates to a compound of formula I, II, III, IV, V, VI, or VII, wherein $R^1$ is OH, $R^2$ is OH, and $R^3$ is H.

In one embodiment, the present disclosure relates to a compound of formula I, II, III, IV, V, VI, or VII, wherein $R^1$ is OH, $R^2$ is OH, and $R^3$ is OH or halogen.

In one embodiment, the present disclosure relates to a compound of formula I, II, III, IV, V, VI, or VII, wherein $R^1$ is OH, $R^2$ is OH, and $R^3$ is $C_1$-$C_6$ alkyl optionally substituted with one or more halogen or OH.

In one embodiment, the present disclosure relates to a compound of formula I, II, III, IV, V, VI, or VII, wherein $R^2$ and $R^3$ taken together with the carbon atom to which they are attached form a carbonyl.

In one embodiment, the present disclosure relates to a compound of formula I, II, III, IV, V, VI, or VII, wherein $R^4$ is H or halogen. In one embodiment, the present disclosure relates to a compound of formula I, II, III, IV, V, VI, or VII, wherein $R^4$ is $C_1$-$C_6$ alkyl optionally substituted with one or more halogen or OH. In one embodiment, $R^4$ is $C_2$-$C_6$ alkenyl or alkynyl. In one embodiment, $R^4$ is methyl, ethyl, or propyl. In one embodiment, $R^4$ is ethyl.

In one embodiment, the present disclosure relates to a compound of formula I, II, III, IV, V, VI, or VII, wherein $R^1$ is OH, $R^2$ is OH, $R^3$ is H, and $R^4$ is methyl, ethyl, or propyl.

In one embodiment, the present disclosure relates to a compound of formula I, II, III, IV, V, VI, or VII, wherein $R^1$ is OH, $R^2$ is OH, $R^3$ is H, and $R^4$ is $C_1$-$C_6$ alkyl optionally substituted with one or more halogen or OH.

In one embodiment, the present disclosure relates to a compound of formula I, II, III, IV, V, VI, or VII, wherein $R^1$ is OH, $R^2$ is OH, $R^3$ is H, and $R^4$ is $C_2$-$C_6$ alkenyl or alkynyl.

In one embodiment, the present disclosure relates to a compound of formula I, II, III, IV, V, VI, or VII, wherein $R^5$ is OH or H. In another embodiment, $R^5$ is $OSO_3H$, $OCOCH_3$, or $OPO_3H_2$. In another embodiment, $R^5$ is halogen.

In one embodiment, the present disclosure relates to a compound of formula I, II, III, IV, V, VI, or VII, wherein $R^1$ is OH, $R^2$ is OH, $R^3$ is H, $R^4$ is methyl, ethyl, or propyl, and $R^5$ is OH or H.

In one embodiment, the present disclosure relates to a compound of formula I, II, III, IV, V, VI, or VII, wherein $R^1$ is OH, $R^2$ is OH, $R^3$ is H, $R^4$ is $C_1$-$C_6$ alkyl optionally substituted with one or more halogen or OH, and $R^5$ is OH or H.

In one embodiment, the present disclosure relates to a compound of formula I, II, III, IV, V, VI, or VII, wherein $R^6$ is OH or H. In another embodiment, the present disclosure relates to a compound of formula I, II, III, IV, V, VI, or VII, wherein $R^6$ is $OSO_3H$, $OCOCH_3$, or $OPO_3H_2$. In another embodiment, $R^6$ is halogen.

In one embodiment, the present disclosure relates to a compound of formula I, II, III, IV, V, VI, or VII, wherein $R^5$ and $R^6$ taken together with the carbon atom to which they are attached form a carbonyl.

In one embodiment, the present disclosure relates to a compound of formula I, II, III, IV, V, VI, or VII, wherein $R^7$ is OH. In one embodiment, $R^7$ is $CO_2H$. In one embodiment, the present disclosure relates to a compound of formula I, II, III, IV, V, VI, or VII, wherein $R^7$ is $OSO_3H$. In a separate embodiment, the present disclosure relates to a compound of formula I, II, III, IV, V, VI, or VII, wherein $R^7$ is $SO_3H$. In another embodiment, the present disclosure relates to a compound of formula I, II, III, IV, V, VI, or VII, wherein $R^7$ is $OSO_2NH_2$ or $SO_2NH_2$. In a separate embodiment, the present disclosure relates to a compound of formula I, II, III, IV, V, VI, or VII, wherein $R^7$ is $OPO_3H_2$, $PO_3H_2$, or C(O)NHOH.

In a separate embodiment, the present disclosure relates to a compound of formula I, II, III, IV, V, VI, or VII, wherein $R^7$ is tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, or 2,4-difluoro-3-hydroxyphenyl. In a separate embodiment, the present disclosure relates to a compound of formula I, II, III, IV, V, VI, or VII, wherein $R^7$ is tetrazolyl. In a separate embodiment, the present disclosure relates to a compound of formula I, II, III, IV, V, VI, or VII, wherein $R^7$ is oxadiazolyl. In a separate embodiment, the present disclosure relates to a compound of formula I, II, III, IV, V, VI, or VII, wherein $R^7$ is thiadiazolyl. In a separate embodiment, the present disclosure relates to a compound of formula I, II, III, IV, V, VI, or VII, wherein $R^7$ is 5-oxo-1,2,4-oxadiazolyl. In one embodiment, the present disclosure relates to a compound of formula I, II, III, IV, V, VI, or VII, wherein $R^7$ is oxazolidine-dionyl. In one embodiment, the present disclosure relates to a compound of formula I, II, III, IV, V, VI, or VII, wherein $R^7$ is thiazolidine-dionyl. In one embodiment, the present disclosure relates to a compound of formula I, II, III, IV, V, VI, or VII, wherein $R^7$ is 2,4-difluoro-3-hydroxyphenyl.

In one embodiment, the present disclosure relates to a compound of formula I, II, III, IV, V, VI, or VII, wherein $R^8$ is H. In one embodiment, $R^8$ is independently is H or OH. In one embodiment, $R^8$ is independently H or halogen. In one embodiment, $R^8$ is independently H or alkyl. In one embodiment, $R^8$ is independently H or alkyl substituted with one or more halogen or OH.

In one embodiment, the present disclosure relates to a compound of formula I, II, III, IV, V, VI, or VII, wherein $R^9$ is H. In one embodiment, $R^9$ is H or OH. In one embodiment, $R^9$ is H or halogen. In one embodiment, $R^9$ is H or alkyl. In one embodiment, $R^9$ is H or alkyl substituted with one or more halogen or OH.

In one embodiment, the present disclosure relates to a compound of formula I, II, III, IV, V, VI, or VII, wherein $R^8$ and $R^9$ are alkyl and taken together with the carbons to which they are attached form a ring of size 3, 4, 5, or 6 atoms.

In one embodiment, the present disclosure relates to a compound of formula I, VI, or VII, wherein $R^{10}$ is H. In one embodiment, $R^{10}$ is H or OH. In one embodiment, $R^{10}$ is H or halogen. In one embodiment, $R^{10}$ is H or alkyl. In one embodiment, $R^{10}$ is H or alkyl substituted with one or more halogen or OH.

In one embodiment, the present disclosure relates to a compound of formula I, VI, or VII, wherein $R^9$ and $R^{10}$ are alkyl and taken together with the carbons to which they are attached form a ring of size 3, 4, 5, or 6 atoms.

In one embodiment, the present disclosure relates to a compound of formula I, II, III, IV, V, VI, or VII, wherein m is 0. In one embodiment, the present disclosure relates to a compound of formula I, II, III, IV, V, VI, or VII, wherein m is 1. In one embodiment, the present disclosure relates to a compound of formula I, II, III, IV, V, VI, or VII, wherein m is 2.

In one embodiment, the present disclosure relates to a compound of formula I, II, III, IV, V, VI, or VII, wherein n is 0. In one embodiment, n is 1.

In one embodiment, the present disclosure relates to a compound of formula I, VI, or VII, wherein p is 0. In one embodiment, p is 1.

In one embodiment, the present disclosure relates to a compound of formula I, wherein the compound is selected from:

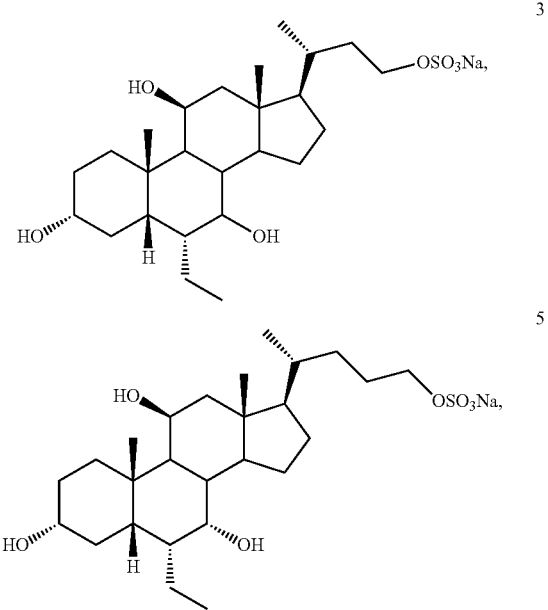

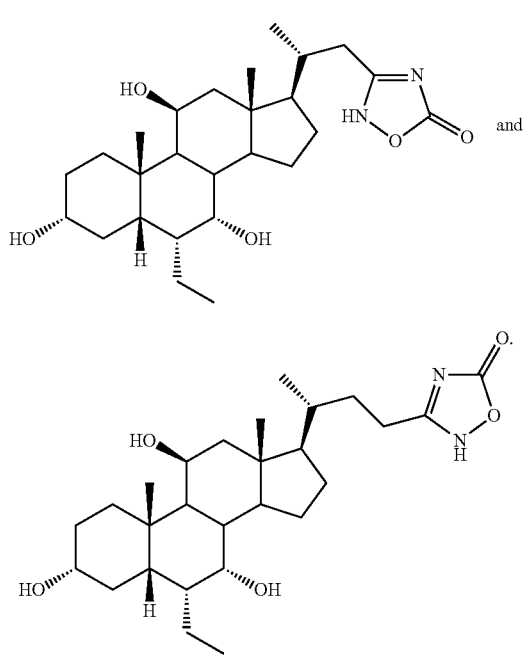

In one of the embodiments, the present disclosure relates to a compound of formula I, wherein the compound is selected from:

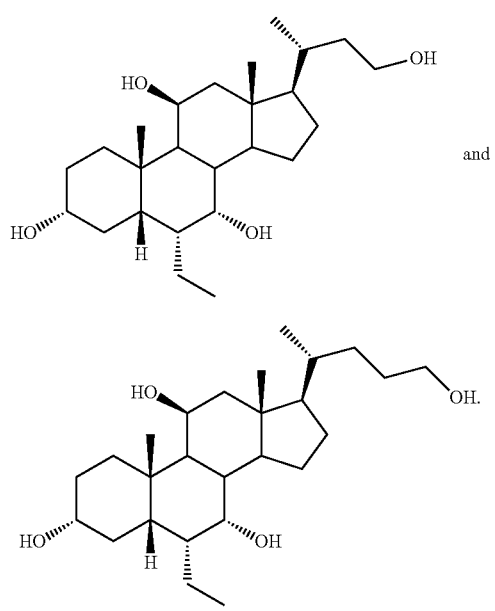

The compounds of the invention have asymmetric centers and can be isolated in optically active or racemic forms. It is well known in the art how to prepare optically active forms, such as by resolution of racemic forms or by synthesis from optically active starting materials. Many geometric isomers of olefins, and the like can also be present in the compounds described herein, and all such stable isomers are contemplated in the present invention. Cis and trans geometric isomers of the compounds of the invention and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention. Furthermore, the invention also includes metabolites of the compounds described herein.

The invention also comprehends isotopically-labelled compounds of the invention, or pharmaceutically acceptable salts, solvates, or amino acid conjugates thereof, which are identical to those recited in formulae of the application and following, but for the fact that one or more atoms are replaced by an atom having an atomic mass or mass number different from the atomic mass or mass number most commonly found in nature. Examples of isotopes that can be incorporated into compounds of the invention, or pharmaceutically acceptable salts, solvates, or amino acid conjugates thereof include isotopes of hydrogen, carbon, nitrogen, fluorine, such as $^3$H, $^{11}$C, $^{14}$C and $^{18}$F.

Tritiated, i.e., $^3$H, and carbon-14, i.e., $^{14}$C, isotopes may be used for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be used in some circumstances. Isotopically labelled compounds of the invention, or pharmaceutically acceptable salts, solvates, or amino acid conjugates thereof can generally be prepared by carrying out the procedures disclosed in the Schemes and/or in the Examples, by substituting a readily available isotopically labelled reagent for a non-isotopically labelled reagent. However, one skilled in the art will recognize that not all isotopes can be included by substitution of the non-isotopically labelled reagent. In one embodiment, compounds of the invention, or pharmaceutically acceptable salts, solvates, or amino acid conjugates thereof are not isotopically labelled. In one embodiment, deuterated compounds of the invention are useful for bioanalytical assays. In another embodiment, compounds of the invention, or pharmaceutically acceptable salts, solvates, or amino acid conjugates thereof are radiolabelled.

Pharmaceutical Compositions

A "pharmaceutical composition" is a formulation containing one or more compounds of the invention in a form suitable for administration to a subject. In one embodiment, the pharmaceutical composition is in bulk or in unit dosage form. It can be advantageous to formulate compositions in dosage unit form for ease of administration and uniformity of dosage. Dosage unit form as used herein refers to physically discrete units suited as unitary dosages for the subject to be treated; each unit containing a predetermined quantity of active reagent calculated to produce the desired therapeutic effect in association with the required pharmaceutical carrier. The specification for the dosage unit forms are dictated by and directly dependent on the unique characteristics of the active reagent and the particular therapeutic effect to be achieved, and the limitations inherent in the art of compounding such an active agent for the treatment of individuals.

Possible formulations include those suitable for oral, sublingual, buccal, parenteral (e.g., subcutaneous, intramuscular, or intravenous), rectal, topical including transdermal, intranasal and inhalation administration. Most suitable means of administration for a particular patient will depend on the nature and severity of the disease being treated or the nature of the therapy being used and on the nature of the active compound, but where possible, oral administration may be used for the prevention and treatment of FXR mediated diseases and conditions. Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in- water or water-in-oil emulsions. Formulations suitable for sublingual or buccal administration include lozenges comprising the active compound and, typically a flavored base, such as sugar and acacia or tragacanth and pastilles comprising the active compound in an inert base, such as gelatin and glycerin or sucrose acacia.

Formulations suitable for parenteral administration typically comprise sterile aqueous solutions containing a predetermined concentration of the active compound; the solution may be isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions may be administered intravenously, they may also be administered by subcutaneous or intramuscular injection.

Formulations suitable for rectal administration may be provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols, and oils. Suitable carriers for such formulations include petroleum jelly, lanolin, polyethyleneglycols, alcohols, and combinations thereof.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example, a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent. Suitable formulations for administration by inhalation include fine particle dusts or mists which may be generated by means of various types of metered dose pressurized aerosols, nebulizers, or insufflators.

For pulmonary administration via the mouth, the particle size of the powder or droplets is typically in the range of 0.5-10 μm, or may be about 1-5 μm to ensure delivery into the bronchial tree. For nasal administration, a particle size in the range of 10-500 μm may be used to ensure retention in the nasal cavity.

Metered dose inhalers are pressurized aerosol dispensers, typically containing a suspension or solution formulation of the active ingredient in a liquefied propellant. During use, these devices discharge the formulation through a valve adapted to deliver a metered volume, typically from 10 to 150 μm, to produce a fine particle spray containing the active ingredient. Suitable propellants include certain chlorofluorocarbon compounds, for example, dichlorodifluoromethane, trichlorofluoromethane, dichlorotetrafluoroethane, and mixtures thereof. The formulation may additionally contain one or more co-solvents, for example, ethanol surfactants, such as oleic acid or sorbitan trioleate, anti-oxidants and suitable flavoring agents.

Nebulizers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulizers consist of the active ingredient in a liquid carrier and comprise up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavouring agents, volatile oils, buffering agents, and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100% w/w of the formulation.

In a further embodiment, the present invention provides a pharmaceutical composition comprising, as active ingredient, a compound of the invention together, and/or in admixture, with at least one pharmaceutical carrier or diluent. These pharmaceutical compositions may be used in the prevention or treatment of the foregoing diseases or conditions.

The carrier is pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient. If desired, other physiologically active ingredients may also be incorporated in the pharmaceutical compositions of the invention.

In addition to the ingredients specifically mentioned above, the formulations of the present invention may include other agents known to those skilled in the art of pharmacy, having regard for the type of formulation in issue. For example, formulations suitable for oral administration may include flavouring agents and formulations suitable for intranasal administration may include perfumes.

In one of the embodiments, the present disclosure provides a pharmaceutical composition comprising the compounds of formula I and Ia-Id and a pharmaceutically acceptable carrier or excipient.

Methods of Treatment

The compounds of the invention are useful for therapy in subjects such as mammals, including humans. In particular, the compounds of the invention are useful in a method of treating or preventing a disease or condition in a subject comprising administering to the subject in need thereof an effective amount of a compound of the invention or a pharmaceutically acceptable salt, solvate, or amino acid conjugate thereof. In one embodiment, the disease or condition is FXR-mediated (e.g., FXR plays a role in the initiation or progress of the disease or condition). In one embodiment, the disease or condition is mediated by decreased FXR activity. In one embodiment, the disease or condition is selected from cardiovascular disease, chronic liver disease, lipid disorder, gastrointestinal disease, renal disease, metabolic disease, cancer, and neurological disease.

In one embodiment, the invention relates to a method of treating or preventing cardiovascular disease in a subject, comprising administering to the subject in need thereof an effective amount of a compound of the invention or a pharmaceutically acceptable salt, solvate, or amino acid conjugate thereof. In one embodiment, the invention relates to a method of treating cardiovascular disease. In one embodiment, cardiovascular disease selected from atherosclerosis, arteriosclerosis, dyslipidemia, hypercholesteremia, hyperlipidemia, hyperlipoproteinemia, and hypertriglyceridemia.

The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "dyslipidemia" refers to abnormal levels of lipoproteins in blood plasma including both depressed and/or elevated levels of lipoproteins (e.g., elevated levels of LDL, VLDL and depressed levels of HDL).

In one embodiment, the invention relates to a method selected from reducing cholesterol levels or modulating cholesterol metabolism, catabolism, absorption of dietary cholesterol, and reverse cholesterol transport in a subject, comprising administering to the subject in need thereof an effective amount of a compound of the invention or a pharmaceutically acceptable salt, solvate, or amino acid conjugate thereof.

In another embodiment, the invention relates to a method of treating or preventing a disease affecting cholesterol, triglyceride, or bile acid levels in a subject, comprising administering to the subject in need thereof an effective amount of a compound of the invention or a pharmaceutically acceptable salt, solvate, or amino acid conjugate thereof.

In one embodiment, the invention relates to a method of lowering triglycerides in a subject, comprising administering to the subject in need thereof an effective amount of a compound of the invention or a pharmaceutically acceptable salt, solvate, or amino acid conjugate thereof.

In one embodiment, the invention relates to a method of treating or preventing a disease state associated with an elevated cholesterol level in a subject, comprising administering to the subject in need thereof an effective amount of a compound of the invention or a pharmaceutically acceptable salt, solvate, or amino acid conjugate thereof. In one embodiment, the invention relates to a method of treating a disease state associated with an elevated cholesterol level in a subject. In one embodiment, the invention relates to a method of preventing a disease state associated with an elevated cholesterol level in a subject. In one embodiment, the disease state is selected from coronary artery disease, angina pectoris, carotid artery disease, strokes, cerebral arteriosclerosis, and xanthoma.

In one embodiment, the invention relates to a method of treating or preventing a lipid disorder in a subject, comprising administering to the subject in need thereof an effective amount of a compound of the invention or a pharmaceutically acceptable salt, solvate, or amino acid conjugate thereof. In one embodiment, the invention relates to a method of treating a lipid disorder. In one embodiment, the invention relates to a method of preventing a lipid disorder.

Lipid disorders are the term for abnormalities of cholesterol and triglycerides. Lipid abnormalities are associated with an increased risk for vascular disease, and especially heart attacks and strokes. Abnormalities in lipid disorders are a combination of genetic predisposition as well as the nature of dietary intake. Many lipid disorders are associated with being overweight. Lipid disorders may also be associated with other diseases including diabetes, the metabolic syndrome (sometimes called the insulin resistance syndrome), underactive thyroid or the result of certain medications (such as those used for anti-rejection regimens in people who have had transplants).

In one embodiment, the invention relates to a method of treating or preventing one or more symptoms of disease affecting lipid metabolism (i.e., lipodystrophy) in a subject, comprising administering to the subject in need thereof an effective amount of a compound of the invention or a pharmaceutically acceptable salt, solvate, or amino acid conjugate thereof. In one embodiment, the invention relates to a method of treating one or more symptoms of a disease affecting lipid metabolism. In one embodiment, the invention relates to a method of preventing one or more symptoms of a disease affecting lipid metabolism.

In one embodiment, the invention relates to a method of decreasing lipid accumulation in a subject, comprising administering to the subject in need thereof an effective amount of a compound of the invention or a pharmaceutically acceptable salt, solvate, or amino acid conjugate thereof.

In one embodiment, the invention relates to a method of treating or preventing chronic liver disease in a subject, comprising administering to the subject in need thereof an effective amount of a compound of the invention or a pharmaceutically acceptable salt, solvate, or amino acid conjugate thereof. In one embodiment, the invention relates to a method of treating chronic liver disease. In one embodiment, the invention relates to a method of preventing chronic liver disease. In one embodiment, the chronic liver disease is selected from primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

In one embodiment, the invention relates to a method of treating or preventing one or more symptoms of cholestasis, including complications of cholestasis in a subject, comprising administering to the subject in need thereof an effective amount of a compound of the invention or a pharmaceutically acceptable salt, solvate, or amino acid conjugate thereof. In one embodiment, the invention relates to a method of treating one or more symptoms of cholestasis. In one embodiment, the invention relates to preventing one or more symptoms of cholestasis.

Cholestasis is typically caused by factors within the liver (intrahepatic) or outside the liver (extrahepatic) and leads to the accumulation of bile salts, bile pigment bilirubin, and lipids in the blood stream instead of being eliminated normally. Intrahepatic cholestasis is characterized by widespread blockage of small ducts or by disorders, such as hepatitis, that impair the body's ability to eliminate bile. Intrahepatic cholestasis may also be caused by alcoholic liver disease, primary biliary cirrhosis, cancer that has spread (metastasized) from another part of the body, primary sclerosing cholangitis, gallstones, biliary colic, and acute cholecystitis. It can also occur as a complication of surgery, serious injury, cystic fibrosis, infection, or intravenous feeding or be drug induced. Cholestasis may also occur as a complication of pregnancy and often develops during the second and third trimesters. Extrahepatic cholestasis is most often caused by choledocholithiasis (Bile Duct Stones), benign biliary strictures (non-cancerous narrowing of the common duct), cholangiocarcinoma (ductal carcinoma), and pancreatic carcinoma. Extrahepatic cholestasis can occur as a side effect of many medications.

A compound of the invention may be used for treating or preventing one or more symptoms of intrahepatic or extrahepatic cholestasis, including without limitation, biliary atresia, obstetric cholestasis, neonatal cholestasis, drug induced cholestasis, cholestasis arising from Hepatitis C infection, chronic cholestatic liver disease such as primary biliary cirrhosis (PBC), and primary sclerosing cholangitis (PSC).

In one embodiment, the invention relates to a method of enhancing liver regeneration in a subject, comprising administering to the subject in need thereof an effective amount of a compound of the invention or a pharmaceutically acceptable salt, solvate, or amino acid conjugate thereof. In one embodiment, the method is enhancing liver regeneration for liver transplantation.

In one embodiment, the invention relates to a method of treating or preventing fibrosis in a subject, comprising administering to the subject in need thereof an effective amount of a compound of the invention or a pharmaceutically acceptable salt, solvate, or amino acid conjugate thereof. In one embodiment, the invention relates to a method of treating fibrosis. In one embodiment, the invention relates to a method of preventing fibrosis.

Accordingly, as used herein, the term fibrosis refers to all recognized fibrotic disorders, including fibrosis due to pathological conditions or diseases, fibrosis due to physical trauma ("traumatic fibrosis"), fibrosis due to radiation damage, and fibrosis due to exposure to chemotherapeutics. As used herein, the term "organ fibrosis" includes but is not limited to liver fibrosis, fibrosis of the kidneys, fibrosis of lung, and fibrosis of the intestine. "Traumatic fibrosis" includes but is not limited to fibrosis secondary to surgery (surgical scarring), accidental physical trauma, burns, and hypertrophic scarring.

As used herein, "liver fibrosis" includes liver fibrosis due to any cause, including but not limited to virally-induced liver fibrosis such as that due to hepatitis B or C virus; exposure to alcohol (alcoholic liver disease), certain pharmaceutical compounds including but not limited to methotrexate, some chemotherapeutic agents, and chronic ingestion of arsenicals or vitamin A in megadoses, oxidative stress, cancer radiation therapy or certain industrial chemicals including but not limited to carbon tetrachloride and dimethylnitrosamine; and diseases such as primary biliary cirrhosis, primary sclerosing cholangitis, fatty liver, obesity, non-alcoholic steatohepatitis, cystic fibrosis, hemochromatosis, auto-immune hepatitis, and steatohepatitis. Current therapy in liver fibrosis is primarily directed at removing the causal agent, e.g., removing excess iron (e.g., in the case of hemochromatosis), decreasing viral load (e.g., in the case of chronic viral hepatitis), or eliminating or decreasing exposure to toxins (e.g., in the case of alcoholic liver disease). Anti-inflammatory drugs such as corticosteroids and colchicine are also known for use in treating inflammation that can lead to liver fibrosis. As is known in the art, liver fibrosis may be clinically classified into five stages of severity (S0, S1, S2, S3, and S4), usually based on histological examination of a biopsy specimen. S0 indicates no fibrosis, whereas S4 indicates cirrhosis. While various criteria for staging the severity of liver fibrosis exist, in general early stages of fibrosis are identified by discrete, localized areas of scarring in one portal (zone) of the liver, whereas later stages of fibrosis are identified by bridging fibrosis (scarring that crosses zones of the liver).

In one embodiment, the invention relates to a method of treating or preventing organ fibrosis in a subject, comprising administering to the subject in need thereof an effective amount of a compound of the invention or a pharmaceutically acceptable salt, solvate, or amino acid conjugate thereof. In one embodiment, the fibrosis is liver fibrosis.

In one embodiment, the invention relates to a method of treating or preventing gastrointestinal disease in a subject, comprising administering to the subject in need thereof an effective amount of a compound of the invention or a pharmaceutically acceptable salt, solvate, or amino acid conjugate thereof. In one embodiment, the invention relates to a method of treating gastrointestinal disease. In one embodiment, the invention relates to a method of preventing gastrointestinal disease. In one embodiment, the gastrointestinal disease is selected from inflammatory bowel disease (IBD), irritable bowel syndrome (IBS), bacterial overgrowth, malabsorption, post-radiation colitis, and microscopic colitis. In one embodiment, the inflammatory bowel disease is selected from Crohn's disease and ulcerative colitis.

In one embodiment, the invention relates to a method of treating or preventing renal disease in a subject, comprising administering to the subject in need thereof an effective amount of a compound of the invention or a pharmaceutically acceptable salt, solvate, or amino acid conjugate thereof. In one embodiment, the invention relates to a method of treating renal disease. In one embodiment, the invention relates to a method of preventing renal disease. In one embodiment, the renal disease is selected from diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease.

In one embodiment, the invention relates to a method of treating or preventing metabolic disease in a subject, comprising administering to the subject in need thereof an effective amount of a compound of the invention or a pharmaceutically acceptable salt, solvate, or amino acid conjugate thereof. In one embodiment, the invention relates to a method of treating renal disease. In one embodiment, the invention relates to a method of preventing renal disease. In one embodiment, the metabolic disease is selected from insulin resistance, hyperglycemia, diabetes mellitus, diabesity, and obesity. In one embodiment, the diabetes mellitus is type I diabetes. In one embodiment, the diabetes mellitus is type II diabetes.

Diabetes mellitus, commonly called diabetes, refers to a disease or condition that is generally characterized by metabolic defects in production and utilization of glucose which result in the failure to maintain appropriate blood sugar levels in the body.

In the case of type II diabetes, the disease is characterized by insulin resistance, in which insulin loses its ability to exert its biological effects across a broad range of concentrations. This resistance to insulin responsiveness results in insufficient insulin activation of glucose uptake, oxidation and storage in muscle and inadequate insulin repression of lipolysis in adipose tissue and of glucose production and secretion in liver. The resulting condition is elevated blood glucose, which is called "hyperglycemia". Uncontrolled hyperglycemia is associated with increased and premature mortality due to an increased risk for microvascular and macrovascular diseases, including retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys), hypertension, cerebrovascular disease, and coronary heart disease. Therefore, control of glucose homeostasis is a critically important approach for the treatment of diabetes.

Insulin resistance has been hypothesized to unify the clustering of hypertension, glucose intolerance, hyperinsulinemia, increased levels of triglyceride and decreased HDL cholesterol, and central and overall obesity. The association of insulin resistance with glucose intolerance, an increase in plasma triglyceride and a decrease in high-density lipoprotein cholesterol concentrations, hypertension, hyperuricemia, smaller denser low-density lipoprotein particles, and higher circulating levels of plasminogen activator inhibitor-1, has been referred to as "Syndrome X". Accordingly, methods of treating or preventing any disorders related to insulin resistance including the cluster of disease states, conditions or disorders that make up "Syndrome X" are provided. In one embodiment, the invention relates to a method of treating or preventing metabolic syndrome in a subject, comprising administering to the subject in need thereof an effective amount of a compound of the invention or a pharmaceutically acceptable salt, solvate, or amino acid conjugate thereof. In one embodiment, the invention relates to a method of treating metabolic syndrome. In another embodiment, the invention relates to a method of preventing metabolic syndrome.

In one embodiment, the invention relates to a method of treating or preventing cancer in a subject, comprising administering to the subject in need thereof an effective amount of a compound of the invention or a pharmaceutically acceptable salt, solvate, or amino acid conjugate thereof. In one embodiment, the invention relates to a method of treating cancer. In one embodiment, the invention relates to a method of preventing cancer. In one embodiment, the cancer is selected from hepatocellular carcinoma, colorectal cancer, gastric cancer, renal cancer, prostate cancer, adrenal cancer, pancreatic cancer, breast cancer, bladder cancer, salivary gland cancer, ovarian cancer, uterine body cancer, and lung cancer. In one embodiment, the cancer is hepatocellular carcinoma. In one embodiment, the cancer is colorectal cancer. In one embodiment, the cancer is gastric cancer. In one embodiment, the cancer is renal cancer. In one embodiment, the cancer is prostate cancer. In one embodiment, the cancer is adrenal cancer. In one embodiment, the cancer is pancreatic cancer. In one embodiment, the cancer is breast cancer. In one embodiment, the cancer is bladder cancer. In one embodiment, the cancer is salivary gland cancer. In one embodiment, the cancer is ovarian cancer. In one embodiment, the cancer is uterine body cancer. In one embodiment, the cancer is lung cancer.

In another embodiment, at least one of an agent selected from Sorafenib, Sunitinib, Erlotinib, or Imatinib is co-administered with the compound of the invention to treat cancer. In one embodiment, at least one of an agent selected from abarelix, aldeleukin, allopurinol, altretamine, amifostine, anastozole, bevacizumab, capecitabine, carboplatin, cisplatin, docetaxel, doxorubicin, erlotinib, exemestane, 5-fluorouracil, fulvestrant, gemcitabine, goserelin acetate, irinotecan, lapatinib ditosylate, letozole, leucovorin, levamisole, oxaliplatin, paclitaxel, panitumumab, pemetrexed disodium, profimer sodium, tamoxifen, topotecan, and trastuzumab is co-administered with the compound of the invention to treat cancer.

Appropriate treatment for cancers depends on the type of cell from which the tumor derived, the stage and severity of the malignancy, and the genetic abnormality that contributes to the tumor.

Cancer staging systems describe the extent of cancer progression. In general, the staging systems describe how far the tumor has spread and puts patients with similar prognosis and treatment in the same staging group. In general, there are poorer prognoses for tumors that have become invasive or metastasized.

In one type of staging system, cases are grouped into four stages, denoted by Roman numerals I to IV. In stage I, cancers are often localized and are usually curable. Stage II and IIIA cancers are usually more advanced and may have invaded the surrounding tissues and spread to lymph nodes. Stage IV cancers include metastatic cancers that have spread to sites outside of lymph nodes.

Another staging system is TNM staging which stands for the categories: Tumor, Nodes, and Metastases. In this system, malignancies are described according to the severity of the individual categories. For example, T classifies the extent of a primary tumor from 0 to 4 with 0 representing a malignancy that does not have invasive activity and 4 representing a malignancy that has invaded other organs by extension from the original site. N classifies the extent of lymph node involvement with 0 representing a malignancy with no lymph node involvement and 4 representing a malignancy with extensive lymph node involvement. M classifies the extent of metastasis from 0 to 1 with 0 representing a malignancy with no metastases and 1 representing a malignancy with metastases.

These staging systems or variations of these staging systems or other suitable staging systems may be used to describe a tumor such as hepatocellular carcinoma. Few options only are available for the treatment of hepatocellular cancer depending on the stage and features of the cancer. Treatments include surgery, treatment with Sorafenib, and targeted therapies. In general, surgery is the first line of treatment for early stage localized hepatocellular cancer. Additional systemic treatments may be used to treat invasive and metastatic tumors.

In one embodiment, the invention relates to a method of treating or preventing gallstones in a subject, comprising administering to the subject in need thereof an effective amount of a compound of the invention or a pharmaceutically acceptable salt, solvate, or amino acid conjugate thereof. In one embodiment, the invention relates to a method of treating gallstones. In one embodiment, the invention relates to a method of preventing gallstones.

A gallstone is a crystalline concretion formed within the gallbladder by accretion of bile components. These calculi are formed in the gallbladder but may distally pass into other parts of the biliary tract such as the cystic duct, common bile duct, pancreatic duct, or the ampulla of Vater. Rarely, in cases of severe inflammation, gallstones may erode through the gallbladder into adherent bowel potentially causing an obstruction termed gallstone ileus. Presence of gallstones in the gallbladder may lead to acute cholecystitis, an inflammatory condition characterized by retention of bile in the gallbladder and often secondary infection by intestinal microorganisms, predominantly *Escherichia coli,* and *Bacteroides* species.

Presence of gallstones in other parts of the biliary tract can cause obstruction of the bile ducts, which can lead to serious conditions such as ascending cholangitis or pancreatitis. In one embodiment, the invention relates to a method of treating or preventing cholesterol gallstone disease in a subject, comprising administering to the subject in need thereof an effective amount of a compound of the invention or a pharmaceutically acceptable salt, solvate, or amino acid conjugate thereof. In one embodiment, the invention relates to a method of treating cholesterol gallstone disease. In one embodiment, the invention relates to a method of preventing cholesterol gallstone disease.

In one embodiment, the invention relates to a method of treating or preventing neurological disease in a subject, comprising administering to the subject in need thereof an effective amount of a compound of the invention or a pharmaceutically acceptable salt, solvate, or amino acid conjugate thereof. In one embodiment, the invention relates to a method of treating neurological disease. In one embodiment, the invention relates to a method of preventing neurological disease. In one embodiment, the neurological disease is stroke.

In one embodiment, the invention relates to a method as described herein and further wherein, the compound is administered by a route selected from oral, parenteral, intramuscular, intranasal, sublingual, intratracheal, inhalation, ocular, vaginal, rectal, and intracerebroventricular. In one embodiment, the route is oral.

In one embodiment, the compound utilized in one or more of the methods described herein is an FXR agonist. In one embodiment, the compound is a selective FXR agonist. In another embodiment, the compound does not activate TGR5. In one embodiment, the compound does not activate other nuclear receptors involved in metabolic pathways (e.g., as measured by an AlphaScreen assay). In one embodiment, such other nuclear receptors involved in metabolic pathways are selected from LXRβ, PXR, CAR, PPARα, PPARδ, PPARγ, RAR, RARα, VDR, TR, PR, RXR, GR, and ER. In one embodiment, the compound induces apoptosis.

In one embodiment, the invention relates to a method of regulating the expression level of one or more genes involved in bile acid homeostasis.

In one embodiment, the invention relates to a method of down regulating the expression level of one or more genes selected from CYP7α1 and SREBP-IC in a cell by administering to the cell a compound of the invention. In one embodiment, the invention relates to a method of up regulating the expression level of one or more genes selected from OSTα, OSTβ, BSEP, SHP, UGT2B4, MRP2, FGF-19, PPARγ, PLTP, APOCII, and PEPCK in a cell by administering to the cell a compound of the invention.

The invention also relates to the manufacture of a medicament for treating or preventing a disease or condition (e.g., a disease or condition mediated by FXR), wherein the medicament comprises a compound of the invention or a pharmaceutically acceptable salt, solvate, or amino acid conjugate thereof. In one embodiment, the invention relates to the manufacture of a medicament for treating or preventing any one of the diseases or conditions described herein above, wherein the medicament comprises a compound of the invention or a pharmaceutically acceptable salt, solvate, or amino acid conjugate thereof.

The invention also relates to a composition for use in a method for treating or preventing a disease or condition (e.g., a disease or condition mediated by FXR), wherein the composition comprises a compound of the invention or a pharmaceutically acceptable salt, solvate, or amino acid conjugate thereof. In one embodiment, the invention relates to a composition for use in a method for treating or preventing any one of the diseases or conditions described herein above, wherein the composition comprises a compound of the invention or a pharmaceutically acceptable salt, solvate, or amino acid conjugate thereof.

The methods of the invention comprise the step of administering an effective amount of a compound of the invention. As used herein, the term an "effective amount" refers to an amount of a compound of the invention which is sufficient to achieve the stated effect. Accordingly, an effective amount of a compound of the invention used in a method for the prevention or treatment of FXR mediated diseases or conditions will be an amount sufficient to prevent or treat the FXR mediated disease or condition.

Similarly, an effective amount of a compound of the invention for use in a method for the prevention or treatment of a cholestatic liver disease or increasing bile flow will be an amount sufficient to increase bile flow to the intestine.

The amount of the compound of the invention which is required to achieve the desired biological effect will depend on a number of factors such as the use for which it is intended, the means of administration, and the recipient, and will be ultimately at the discretion of the attendant physician or veterinarian. In general, a typical daily dose for the treatment of a FXR mediated disease and condition, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including the prevention and treatment of cholestatic liver diseases.

In one of the embodiments, the present disclosure proves a method of treating or preventing a disease or condition in a subject in need thereof comprising administering an effective amount of the compound of formula I or Ia-Id or a pharmaceutically acceptable salt, solvate, or amino acid conjugate thereof, and wherein the disease or condition is mediated by FXR.

In one of the embodiments, the present disclosure proves a method of treating or preventing a disease or condition in a subject in need thereof comprising administering an effective amount of the compound of formula I or Ia-Id, wherein the disease is selected from cardiovascular disease, chronic liver disease, lipid disorder, gastrointestinal disease, renal disease, metabolic disease, cancer, and neurological disease.

In one of the embodiments, the present disclosure proves a method of treating or preventing a disease or condition in a subject in need thereof comprising administering an effective amount of the compound of formula I or Ia-Id, wherein the disease is cardiovascular disease selected from atherosclerosis, arteriosclerosis, dyslipidemia, hypercholesteremia, hyperlipidemia, hyperlipoproteinemia, and hypertriglyceridemia.

In one of the embodiments, the present disclosure proves a method of treating or preventing a disease or condition in a subject in need thereof comprising administering an effective amount of the compound of formula I or Ia-Id, wherein the disease is chronic liver disease selected from primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

In one of the embodiments, the present disclosure proves a method of treating or preventing a disease or condition in a subject in need thereof comprising administering an effective amount of the compound of formula I or Ia-Id, wherein the disease is gastrointestinal disease selected from inflammatory bowel disease (IBD), irritable bowel syndrome (IBS), bacterial overgrowth, malabsorption, post-radiation colitis, and microscopic colitis.

In one of the embodiments, the present disclosure proves a method of treating or preventing a disease or condition in a subject in need thereof comprising administering an effective amount of the compound of formula I or Ia-Id, wherein the inflammatory bowel disease is Crohn's disease or ulcerative colitis.

In one of the embodiments, the present disclosure proves a method of treating or preventing a disease or condition in a subject in need thereof comprising administering an effective amount of the compound of formula I or Ia-Id, wherein the disease is renal disease selected from diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease.

In one of the embodiments, the present disclosure proves a method of treating or preventing a disease or condition in a subject in need thereof comprising administering an effective amount of the compound of formula I or Ia-Id, wherein the disease is metabolic disease selected from insulin resistance, hyperglycemia, diabetes mellitus, diabesity, and obesity.

In one of the embodiments, the present disclosure proves a method of treating or preventing a disease or condition in a subject in need thereof comprising administering an effective amount of the compound of formula I or Ia-Id, wherein the disease is cancer selected from hepatocellular carcinoma, colorectal cancer, gastric cancer, renal cancer, prostate cancer, adrenal cancer, pancreatic cancer, breast cancer, bladder cancer, salivary gland cancer, ovarian cancer, uterine body cancer, and lung cancer.

Synthesis of the Compounds of the Invention

The following Schemes and Examples are illustrative and should not be interpreted in any way so as to limit the scope of the invention.

The present invention provides a method of synthesizing compounds of Formula I,

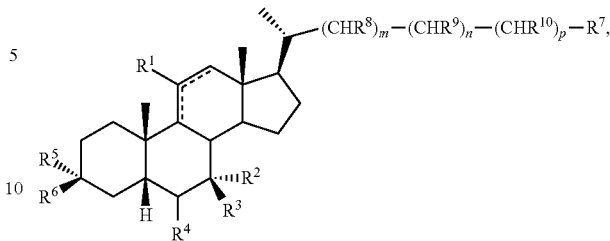

(I)

or a pharmaceutically acceptable salt, solvate, or amino acid conjugate thereof, wherein $R^1$-$R^{10}$, m, n, p, and - - - are as described herein.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, solvate or amino acid conjugate thereof.

The compounds of the invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5th edition, John Wiley & Sons: New York, 2001; and Greene, T. W., Wuts, P. G. M., Protective Groups in Organic Synthesis, 3rd edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

All the abbreviations used in this application are found in "Protective Groups in Organic Synthesis" by John Wiley & Sons, Inc., or the MERCK INDEX by MERCK & Co., Inc., or other chemistry books or chemicals catalogues by chemicals vendor such as Aldrich, or according to usage know in the art.

The synthetic process to afford compounds of the invention can be used according to the procedures set forth below in Schemes 1-6.

Pharmacology of the Compounds of the Invention

In general, the potential of a compound of the invention as a drug candidate may be tested using various assays known in the art. For example, for the in-vitro validation of FXR, its activity and selectivity can be evaluated using AlphaScreen (biochemical assay); gene expression can be evaluated using RT-PCR (FXR target gene); and cytotoxicity (e.g., HepG2) can be evaluated using ATP content LDH release, and Caspase-3 activation. For the in-vitro validation for TGR5, its activity and selectivity can be evaluated using HTR-FRET (cell-based assay); gene expression can be evaluated using RT-PCR (TGR5 target gene (i.e., cFOS)); and cytotoxicity (e.g., HepG2) can be evaluated using ATP content, LDH release, and Caspase-3 activation. The following compounds can be used as controls in the examples below.

As used herein Compound A is

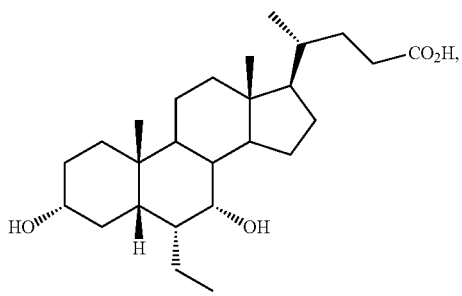 [SMILES: CC[C@H]1[C@@H](O)C2C3CC[C@H]([C@H](C)CCC(=O)O)[C@@]3(C)CCC2[C@@]2(C)CC[C@@H](O)C[C@@H]12]

which is also known as obeticholic acid, INT-747, 6-ECDCA, 6-alpha-ethyl chenodeoxycholic acid, or 6α-ethyl-3α,7α-dihydroxy-5β-cholan-24-oic acid.

As used herein Compound B is

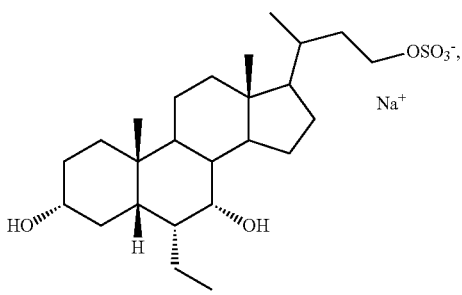

which is also known as INT-767 or 6α-ethyl-3α,7α,23-trihydroxy-24-nor-5β-cholan-23-sulphate sodium salt.

As used herein, Compound C is

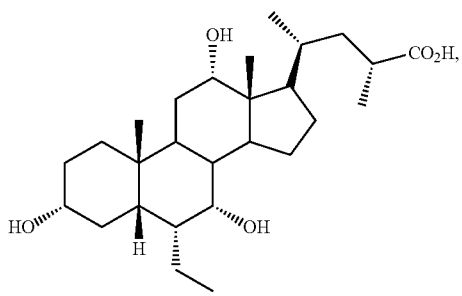

which is also known as INT-777 or 6α-ethyl-23(S)-methyl-3α,7α,12α trihydroxy-5β-cholan-24-oic acid.

As used herein, Compound D

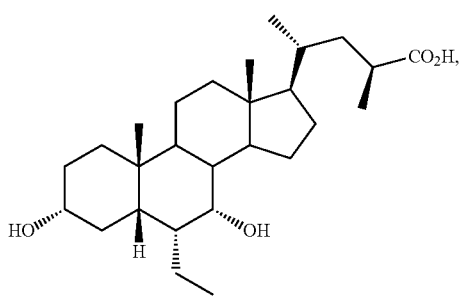 [SMILES: CC[C@H]1[C@@H](O)C2C3CC[C@H]([C@H](C)C[C@H](C)C(=O)O)[C@@]3(C)CCC2[C@@]2(C)CC[C@@H](O)C[C@@H]12]

which is also known as 6α-ethyl-23(R)-methyl chenodeoxycholic acid, and S-EMCDCA.

As used herein, Compound E is

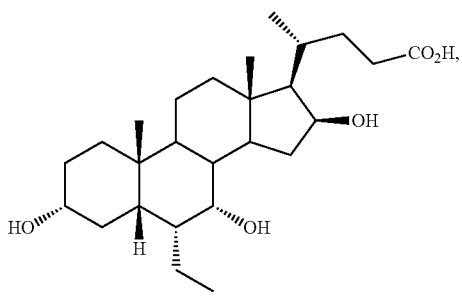 [SMILES: CC[C@H]1[C@@H](O)C2C3C[C@H](O)[C@H]([C@H](C)CCC(=O)O)[C@@]3(C)CCC2[C@@]2(C)CC[C@@H](O)C[C@@H]12]

As used herein, cholic acid is

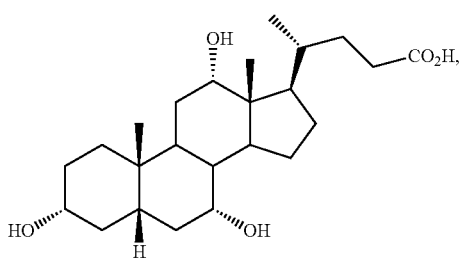 [SMILES: C[C@H](CCC(=O)O)[C@H]1CCC2C3C(C[C@H](O)[C@@]21C)[C@@]1(C)CC[C@@H](O)C[C@H]1C[C@H]3O]

which is also known as CA.

As used herein, chenodeoxycholic acid is

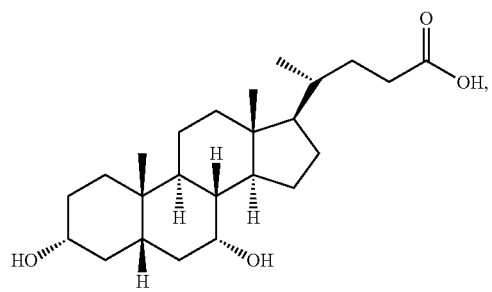

which is also known as CDCA.

As used herein, ursodeoxycholic acid is

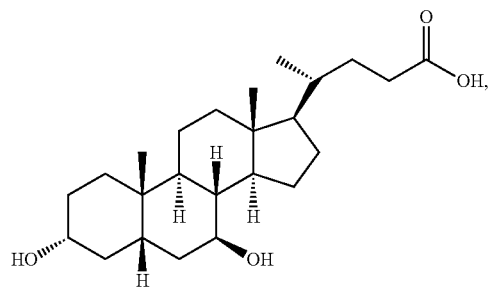

which is also known as UDCA.

As used herein taurochenodeoxycholic acid is

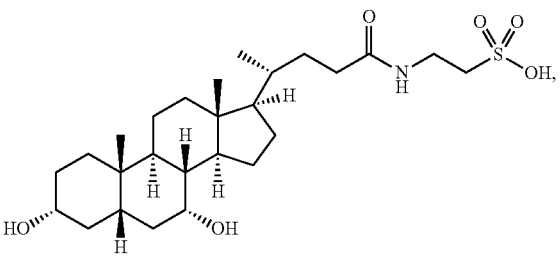

which is also known as TCDCA.

As used herein, tauroursodeoxycholic acid is

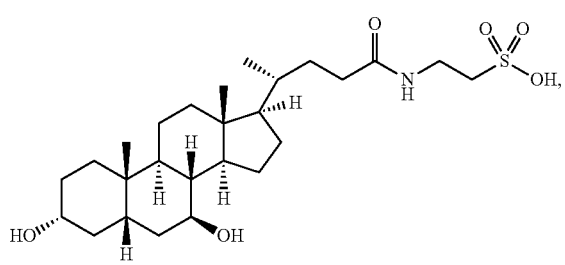

which is also known as TUDCA.

As used herein, lithocholic acid is

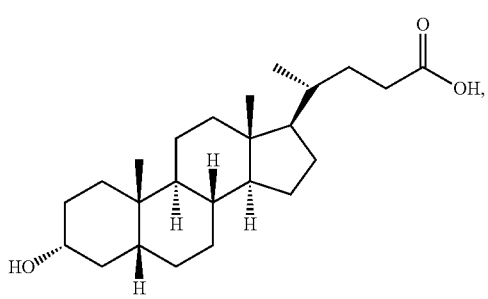

which is also known as LCA.

EXAMPLES

Example 1

Synthesis of 3α,7α,11β-trihydroxy-6α-ethyl-24-nor-5β-cholan-23-oic acid (Compound 1)

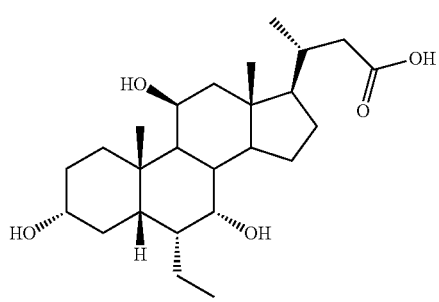 [SMILES: CC[C@H]1[C@@H](O)C2C3CC[C@H]([C@H](C)CC(=O)O)[C@@]3(C)C[C@H](O)C2[C@@]2(C)CC[C@@H](O)C[C@@H]12]

Compound 1 was prepared according to the procedures described in Scheme 1 and from 6-ethyl-cholic acid (6-ECA, Compound A1) as the starting material. Compound A1 was prepared by methods known in the art. For example, Compound A1 can be prepared by the procedures described in Pellicciari, R., et al., J. Med. Chem. 2009, 52, 7958-7961.

Scheme 1.

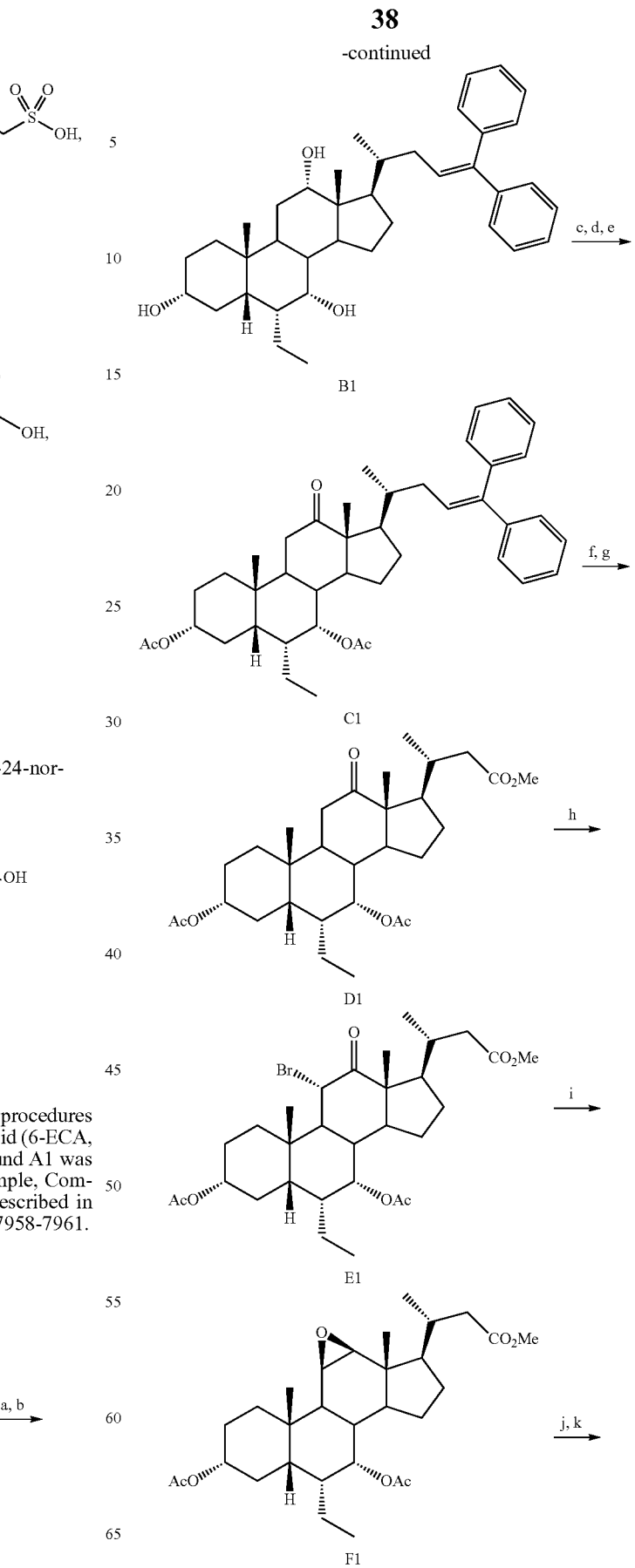
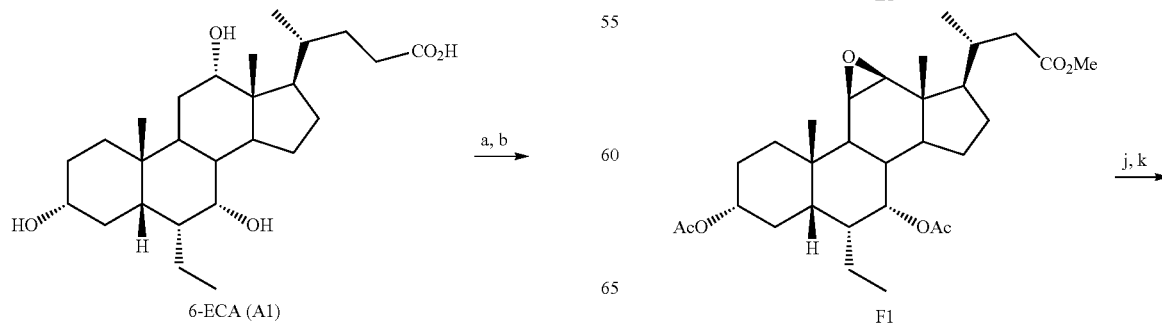

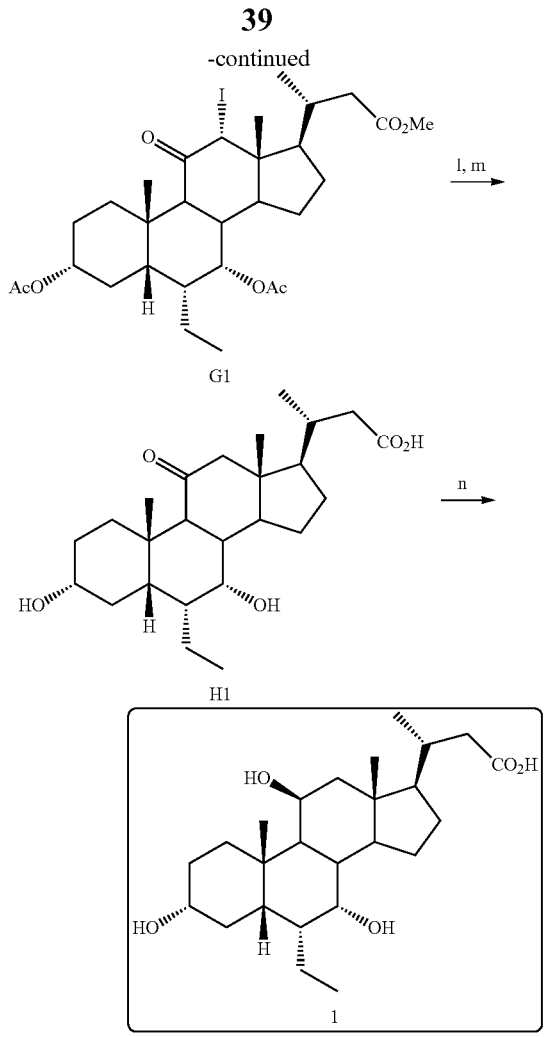

Scheme 1. Reagents and conditions: a) MeOH, p-TSA, ultrasound; b) PhMgBr in Et$_2$O, THF, reflux; HCl, EtOH, reflux then room temperature; c) MeOAc, p-TSA, reflux; d) PCC, CH$_2$Cl$_2$; e) Ac$_2$O, Bi(OTf)$_3$, CH$_2$Cl$_2$; f) NaIO$_4$, H$_2$O, H$_2$SO$_4$, RuCl$_3$, MeCN, EtOAc; g) MeOH, p-TSA, reflux; h) Br$_2$, benzene, 30° C.; i) NaBH$_4$, NaOAc, pyridine, 25° C.; j) HI, AcOH; k) CrO$_3$, AcOH; l) Zn dust, NaOAc, AcOH, reflux; m) NaOH, MeOH, H$_2$O, reflux; and n) NaBH$_4$, THF, H$_2$O.

3α,7α,12α-Trihydroxy-6α-ethyl-5β-bisnorcholanyl-diphenylethylene (Compound B1)

A solution of Compound A1 (8 g, 18.32 mmol) and para-toluenesulphonic acid (p-TSA) (352 mg, 1.83 mmol) in MeOH (200 mL) was treated under ultrasound for 3 h. The mixture was concentrated under vacuum, diluted with CHCl$_3$, and washed with a saturated solution of NaHCO$_3$. The organic phase was washed with brine, dried over anhydrous Na$_2$SO$_4$, and concentrated under reduced pressure to obtain 7.96 g of methyl 6α-ethylcholate derivative. The methyl ester thus formed (17.66 mmol) was dissolved in freshly distilled THF (80 mL) and the mixture was warmed up to 50° C. under magnetic stirring and argon atmosphere. PhMgBr in Et$_2$O (176.6 mmol) was then added dropwise and the resulting mixture was refluxed for 14 h. The suspension was treated with aqueous HCl (50 mL) and extracted with EtOAc (3×120 mL). The collected organic layers were washed with a saturated solution of NaHCO$_3$, brine, dried over anhydrous Na$_2$SO$_4$ and concentrated under reduced pressure. The resulting oil was treated with 160 mL of HCl:EtOH (3:1, v/v), refluxed for 3 h and stirred at room temperature overnight. EtOH was removed under vacuum and the mixture was extracted with EtOAc (3×100 mL). The combined organic phases were washed with a saturated solution of NaHCO$_3$, brine, dried over anhydrous Na$_2$SO$_4$, and concentrated under reduced pressure. The crude was purified by silica gel flash chromatography to obtain the desired product B1 in 76% yield (7.7 g, 13.85 mmol).

3α,7α-Diacetoxy-12-oxo-6α-ethyl-5β-bisnorcholanyldiphenylethylene (Compound C1)

A solution of Compound B1 (7.7 g, 13.85 mmol) and p-TSA (266 mg, 1.38 mmol) in MeOAc (70 mL) was refluxed for 2 d. The mixture was washed with a saturated solution of NaHCO$_3$, brine, dried over anhydrous Na$_2$SO$_4$, and concentrated under vacuum to give 8.15 g of 3α-acetoxy-7α,12α-dihydroxy-6α-ethyl-5β-bisnorcholanyldiphenylethylene. The crude (8.18 g) was dissolved in dry CH$_2$Cl$_2$ (270 mL). Pyridinium chlorochromate (PCC) (2.95 g) was added and the mixture was stirred for 4 h. The resulting brown suspension was filtered, treated with aqueous HCl, and the organic layer was washed with H$_2$O and brine. After being dried over anhydrous Na$_2$SO$_4$ and concentrated under reduced pressure, the crude was purified by silica gel flash chromatography to obtain 5.6 g (9.39 mmol) of the desired 12-oxo derivative. The intermediate was then dissolved in CH$_2$Cl$_2$ (80 mL), treated with Ac2O (4.5 mL, 46.95 mmol), Bi(OTf)$_3$ (306 mg, 0.469 mmol), and stirred for 40 min. The suspension thus obtained was filtered and acidified with aqueous HCl. The organic phase was washed with H$_2$O and brine, dried over anhydrous Na$_2$SO$_4$ and concentrated under vacuum. The crude was filtered on silica gel pad to obtain 5.3 g (8.29 mmol) of Compound C1 in 60% yield.

Methyl 3αa,7α-diacetoxy-12-oxo-6α-ethyl-24-nor-5β-cholan-23-oate (Compound D1)

NaIO$_4$ (15.97 g, 74.66 mmol) was stirred in 15 mL of H$_2$O and 2 N H$_2$SO$_4$ (2.4 mL). After 1 h the solution was cooled at 0° C., RuCl$_3$ (85.9 mg, 0.415 mmol) was added and the mixture was magnetically stirred for 1 h. MeCN (23.5 mL) was added as phase transfer and after 5 min a solution of Compound C1 (5.3 g, 8.29 mmol) in EtOAc (32.5 mL) was dropped and allowed to react for 1 h. The mixture was filtered off, poured into H$_2$O, and extracted with EtOAc (3×100 mL). The combined organic layers were washed with brine, dried over Na$_2$SO$_4$, and concentrated under reduced pressure. The resulting residue was filtered on silica gel pad to give 5.33 g of 6α-ethyl-24-nor-cholic acid derivative which was dissolved in MeOH (90 mL), treated under ultrasound in the presence of p-TSA (160 mg, 0.829 mmol) for 3 h and then refluxed for 1 h. The mixture was concentrated under vacuum, diluted with CHCl$_3$, and washed with a saturated solution of NaHCO$_3$. The organic phase was washed with brine, dried over anhydrous Na$_2$SO$_4$, and concentrated under vacuum. The crude was purified by silica gel flash chromatography to give Compound D1 in 86% yield (3.73 g, 7.19 mmol).

Methyl 11α-bromine-3α,7α-diacetoxy-12-oxo-6α-ethyl-24-nor-5β-cholan-23-oate (Compound E1)

A solution of Br$_2$ in anhydrous benzene (2 M, 4.67 mL) was added dropwise to a solution of Compound D1 (3.73 g, 7.19 mmol) in benzene (156 mL). The resulting red solution was allowed to react at 30° C. under argon atmosphere for 3 days. The mixture was poured into aqueous solution of Na$_2$S$_2$O$_3$ and the yellow suspension extracted with EtOAc (3×100 mL). The collected organic layers were washed with H$_2$O and brine, dried over anhydrous Na$_2$SO$_4$, and concentrated under vacuum. The crude was purified by silica gel flash chromatography to obtain Compound E1 as white-yellow solid (2.65 g, 4.43 mmol).

Methyl 3α,7α-diacetoxy-11β,12β-oxo-6α-ethyl-24-nor-5β-cholan-23-oate (Compound F1)

NaOAc (2.65 g, 32.81 mmol) and NaBH$_4$ (808 mg, 21.27 mmol) were added to a solution of Compound E1 (2.65 g, 4.43 mmol) in freshly distilled pyridine (27.5 mL) and the suspension was allowed to react at 25° C. under Na atmosphere for 14 h. The mixture was treated with aqueous HCl and extracted with EtOAc (3×80 mL). The combined organic phases were washed with H$_2$O, brine, and dried under vacuum. The crude oil was purified by silica gel flash chromatography to obtain 1.52 g (2.85 mmol) of Compound F1 in 64% yield.

Methyl 12α-iodine-3α,7α-diacetoxy-11-oxo-6α-ethyl-24-nor-5β-cholan-23-oate (Compound G1)

To a solution of Compound F1 (1.52 g, 2.85 mmol) in AcOH (40 mL), HI 57% (3.6 g, 28.5 mmol) was added dropwise and the mixture was allowed to react at room temperature for 30 min. The mixture was treated with an aqueous solution of NaHSO$_3$, poured into iced H$_2$O, filtered, and the resulting solid dissolved in AcOH (35 mL). A solution of CrO$_3$ (1.4 g, 14.3 mmol) in AcOH (40 mL) and H$_2$O (8 mL) was added dropwise and the mixture stirred for 45 min. The reaction was quenched with an aqueous solution of NaHSO$_3$ and poured into iced water. The suspension was filtered and the solid dissolved in CHCl$_3$. The solution was then washed with H$_2$O, brine, dried over anhydrous Na$_2$SO$_4$, and concentrated under reduced pressure. The crude was purified by silica gel flash chromatography to give Compound G1 as pure product (1 g, 1.67 mmol).

3α,7α-Dihydroxy-11-oxo-6α-ethyl-24-nor-5β-cholan-23-oic acid (Compound H$_1$)

NaOAc (3.8 g, 46.76 mmol) and Zn dust (3.8 g, 58.45 mmol) were added to a solution of Compound G1 (1 g, 1.69 mmol) in AcOH (30 mL) and the resulting suspension was refluxed for 2 h. The mixture was filtered and the filtrate treated with H$_2$O at 0° C. up to precipitation. The precipitate was dissolved in CHCl$_3$ and the aqueous phase extracted with CHCl$_3$ (3×50 mL). The collected organic layers were treated with a saturated solution of NaHCO$_3$, washed with brine, dried over anhydrous Na$_2$SO$_4$ and then concentrated under vacuum. The crude (880 mg) was dissolved in MeOH and H$_2$O, NaOH (25.45 mmol) was added and the mixture was refluxed for 36 h. The resulting solution was concentrated under reduced pressure, diluted with H$_2$O and treated with aqueous HCl. It was extracted with CHCl$_3$ (3×50 mL) and the combined organic phases were washed with brine, dried over anhydrous Na$_2$SO$_4$, and concentrated under vacuum to give Compound H1.

3α,7α,11β-Trihydroxy-6α-ethyl-24-nor-5β-cholan-23-oic acid (Compound 1)

To a solution of Compound H1 (650 mg, 1.54 mmol) in THF:H$_2$O (33 mL, 4:1 v/v), NaBH$_4$ (407 mg, 10.78 mmol) was added portionwise at 0° C. and the resulting suspension was allowed to react at room temperature for 5 h. After being treated with H$_2$O and aqueous HCl, the crude reaction mixture was extracted with CHCl$_3$ (3×50 mL). The collected organic layers were washed with brine, dried over anhydrous Na$_2$SO$_4$, and concentrated under vacuum to give 650 mg of Compound 1 (1.69 mmol, quantitative yield) (9% overall yield from 1).

Compound 1: $^1$H-NMR (400 MHz, CD3OD): δ 0.89 (3H, t, J=7.33 Hz, CH$_3$-25), 0.94 (3H, s, CH$_3$-18), 1.04 (3H, d, J=5.46 Hz, CH$_3$-21), 1.13 (3H, s, CH$_3$-19), 3.30-3.35 (1H, m, CH-3), 3.71 (1H, s, CH-7), 4.19 (1H, s, CH-11). $^{13}$C-NMR (400 MHz, CD$_3$OD): 12.0, 14.6, 19.9, 23.5, 24.6, 27.7, 29.1, 31.9, 34.7, 35.2, 36.4, 36.9, 38.3 (2×), 42.6 (2 x), 42.8, 49.5, 49.9, 52.2, 57.9, 69.0, 71.4, 73.3, 177.7.

Example 2

Synthesis of 3α,7α,11β-trihydroxy-6α-ethyl-24-nor-5β-cholan-23-ol (Compound 2)

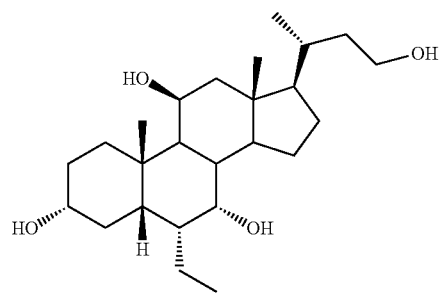 [SMILES: CC[C@H]1[C@@H](O)C2C3CC[C@H]([C@H](C)CCO)[C@@]3(C)C[C@H](O)C2[C@@]2(C)CC[C@@H](O)C[C@@H]12]

Compound 2 was prepared according to the procedures set forth in Scheme 2. Compound 2 was prepared from Compound 1 as the starting material.

Example 3

Synthesis of 3α,7α,11β,23-tetrahydroxy-6α-ethyl-24-nor-5β-cholan-23-O-sulphate sodium salt (Compound 3)

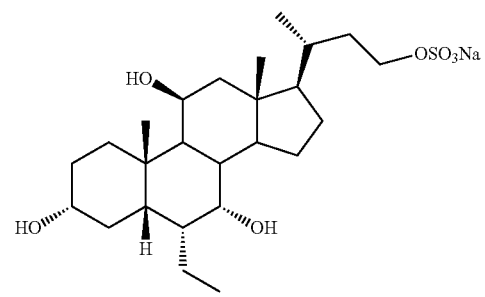

Compound 3 was prepared according to the procedures set forth in Scheme 2. Compound 3 was prepared from Compound 1 as the starting material.

Scheme 2.

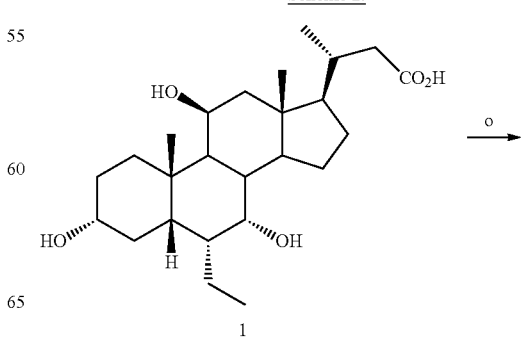

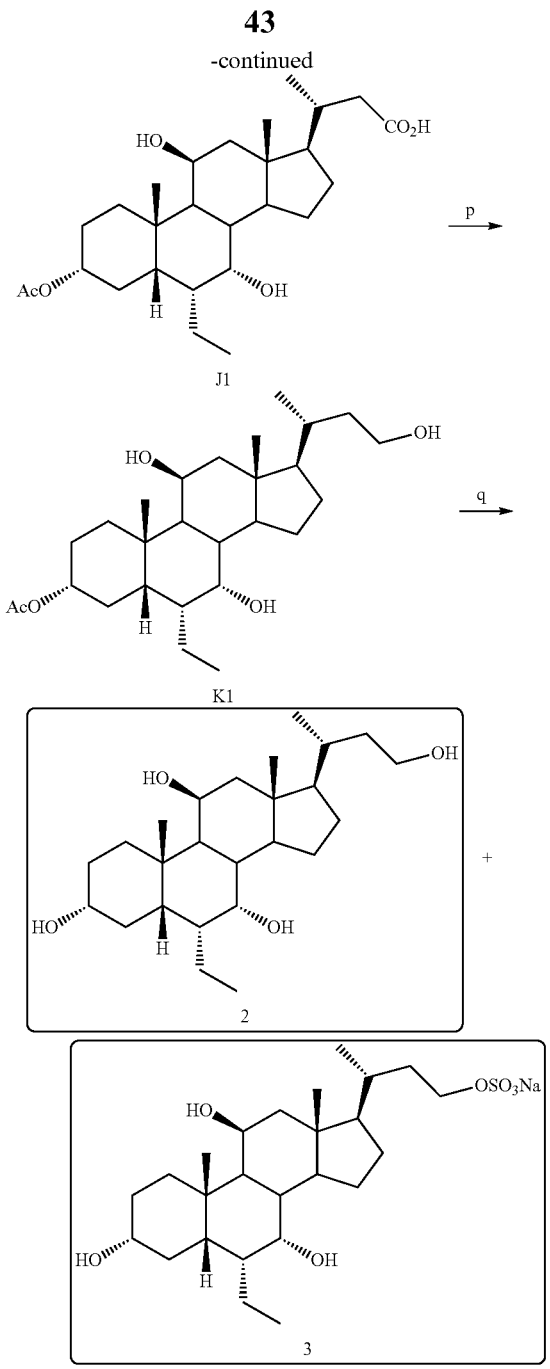

Scheme 2. Reagents and conditions: o) Ac₂O, THF, reflux; p) EtCOCl, Et₃N, THF; NaBH₄, THF, H₂O; and q) PyrSO₃, pyridine; NaOH, MeOH, H₂O, reflux.

3α-Acetoxy-7α,11β-dihydroxy-6α-ethyl-24-nor-5β-cholan-23-oic acid (Compound J1)

Ac₂O (2.08 mL, 21.6 mmol) was added to a solution of Compound 1 (460 mg, 1.08 mmol) in THF (35 mL) and the mixture was refluxed for 18 h. The resulting solution was treated with aqueous HCl extracted with EtOAc (3×30 mL). The combined organic phases were washed with H₂O, brine, dried over anhydrous Na₂SO₄ and concentrated under reduced pressure. The crude was purified by silica gel flash chromatography to obtain Compound J1 (255 mg, 0.548 mmol).

3α-Acetoxy-7α,11β-dihydroxy-6α-ethyl-24-nor-5β-cholan-23-ol (Compound K1)

A solution of Compound J1 (250 mg, 0.538 mmol), EtCOCl (0.51 mL, 5.326 mmol), and Et₃N (0.81 mL, 5.649 mmol) in THF (7.5 mL) was allowed to react for 14 h at room temperature. The reaction mixture was then filtered, treated with a suspension of NaBH₄ (306 mg, 8.07 mmol) in H₂O (2.5 mL) and stirred for 2 h. The mixture was acidified with aqueous HCl and extracted with EtOAc (3×30 mL). The combined organic extracts were washed with brine, dried over Na₂SO₄, and concentrated under vacuum. The crude was filtered on silica gel pad to give Compound K1 (150 mg, 0.333 mmol).

3α,7α,11β-trihydroxy-6α-ethyl-24-nor-5β-cholan-23-ol (2) and 3α,7α,11β,23-tetrahydroxy-6α-ethyl-24-nor-5β-cholan-23-O-sulphate sodium salt (Compound 3)

To a solution of Compound K1 (150 mg, 0.333 mmol) in pyridine (6 mL), was added PyrSO₃ (133 mg, 0.832 mmol) and the resulting mixture was stirred under argon atmosphere for 24 h. The reaction mixture was diluted with H₂O (2 mL) and concentrated at reduced pressure to remove pyridine. The residue was treated with a solution of NaOH (200 mg, 4.995 mmol) in MeOH:H₂O (10 mL) and refluxed overnight. The mixture was dried under vacuum to remove MeOH, diluted with H₂O (2 mL), and washed with Et₂O (3×20 mL): the combined ethereal phases were washed with brine, dried over anhydrous Na₂SO₄, and purified by flash chromatography to give the 3α,7α,11β-trihydroxy-6α-ethyl-24-nor-5β-cholan-23-ol (2) as pure white solid (55 mg, 0.134 mmol). The aqueous alkaline phase was filtered on a reverse phase RP-18 pad to obtain Compound 3 as pure white solid (60 mg, 0.117 mmol).

Compound 2: ¹H-NMR (400 MHz, CDCl₃): δ 0.88-0.92 (6H, m, CH₃-25, CH₃-18), 0.97 (3H, d, J=6.5 Hz, CH₃-21), 1.14 (3H, s, CH₃-19), 3.40-3.47 (1H, m, CH-3), 3.62-3.72 (2H, m, CH₂-23), 3.80 (1H, s, CH-7), 4.25 (1H, d, J=2.72 Hz, CH-11). ¹³C-NMR (400 MHz, CDCl₃): 11.6, 14.4, 18.8, 22.2, 23.8, 27.0, 28.0, 31.1, 32.9, 34.1, 35.3, 35.7, 36.4, 37.1, 38.8, 40.6, 41.6, 47.7, 48.8, 50.9, 56.8, 60.7, 68.8, 71.0, 72.3.

Compound 3: ¹H-NMR (400 MHz, CD₃OD): δ 0.90-0.94 (6H, m, CH₃-25, CH₃-18), 1.04 (3H, d, J=6.4 Hz, CH₃-21), 1.15 (3H, s, CH₃-19), 3.32-3.40 (1H, m, CH-3), 3.74 (1H, s, CH-7), 4.02-4.08 (2H, m, CH₂-23), 4.21 (1H, s, CH-11). ¹³C-NMR (400 MHz, CD₃OD): 12.0, 14.6, 19.1, 23.5, 24.7, 27.7, 29.1, 31.9, 34.3, 34.8, 36.4, 36.5, 36.9, 38.3 (×2), 42.6, 42.8, 49.5, 50.0, 52.2, 58.2, 67.2, 69.0, 71.4, 73.3.

Example 4

Synthesis of 3α,7α,11β-trihydroxy-6α-ethyl-5β-cholan-24-ol (Compound 4)

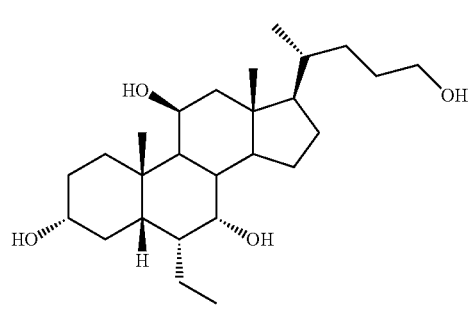 [SMILES: CC[C@H]1[C@@H](O)C2C3CC[C@H]([C@H](C)CCCO)[C@@]3(C)C[C@H](O)C2[C@@]2(C)CC[C@@H](O)C[C@@H]12]

4 was prepared according to the procedures set forth in Scheme 3. The synthesis of 4 was prepared from Compound L1 as the starting material. Compound L1 was prepared by methods known in the art. For example, Compound L1 can be prepared by the procedures described in U.S. Publication No. 2014/0371190.

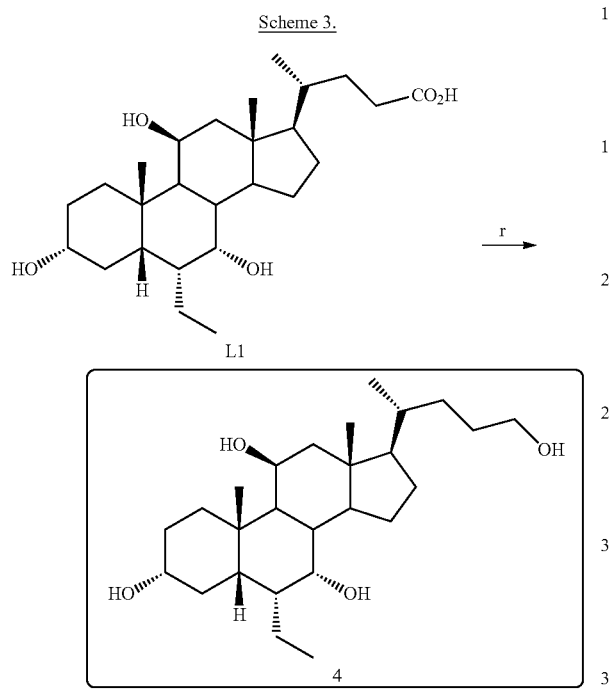

Scheme 3. Reagents and conditions: r) LiAlH₄, THF, from 0 °C. to room temperature 3α,7α,11β-Trihydroxy-6αa-ethyl-5β-cholan-24-ol (Compound 4)

A solution of Compound L1 (25 mg, 0.057 mmol) in THF (2 mL) was added dropwise to a suspension of LiAlH₄ (21.8 mg, 0.572 mmol) in THF (1 mL) cooled at 0° C. The resulting mixture was allowed to react under argon atmosphere and room temperature for 12 h. The suspension was diluted with EtOAc (5 mL), treated firstly with H₂O, then with aqueous HCl, and finally extracted with EtOAc (3×5 mL). The combined organic layers were washed with brine, dried over anhydrous Na₂SO₄, and concentrated under vacuum. The crude was purified by flash chromatography to give Compound 4 as pure white solid (21 mg, 0.051 mmol, 90% yield).

Compound 4: $^1$H-NMR (400 MHz, CD$_3$OD): δ 0.88-0.92 (6H, m, CH$_3$-26, CH$_3$-18), 1.00 (3H, d, J=6.25 Hz, CH$_3$-21), 1.14 (3H, s, CH$_3$-19), 3.31-3.40 (1H, m, CH-3), 3.48-3.55 (2H, m, CH$_2$-24), 3.73 (1H, s, CH-7), 4.19 (1H, s, CH-11). $^{13}$C-NMR (400 MHz, CD$_3$OD): 12.0, 14.6, 19.2, 23.5, 24.7, 27.7, 29.1, 30.3, 31.9, 33.2, 34.8, 36.4, 36.9, 37.2, 38.3 (×2), 42.6, 42.7, 49.5, 50.1, 52.2, 58.1, 63.6, 69.1, 71.4, 73.3.

Example 5

Synthesis of 3α,7α,11β-rihydroxy-6α-ethyl-5β-cholan-24-O-sulphate, sodium salt (Compound 5)

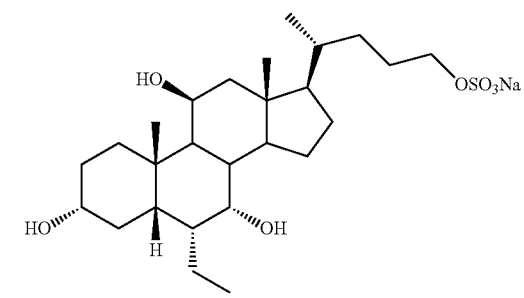

Compound 5 was prepared according to the procedures set forth in Scheme 4. The synthesis of Compound 5 was prepared from Compound M1 as the starting material. Compound M1 was prepared by methods known in the art. For example, Compound M1 can be prepared by the procedures described in U.S. Publication No. 2014/0371190.

Scheme 4.

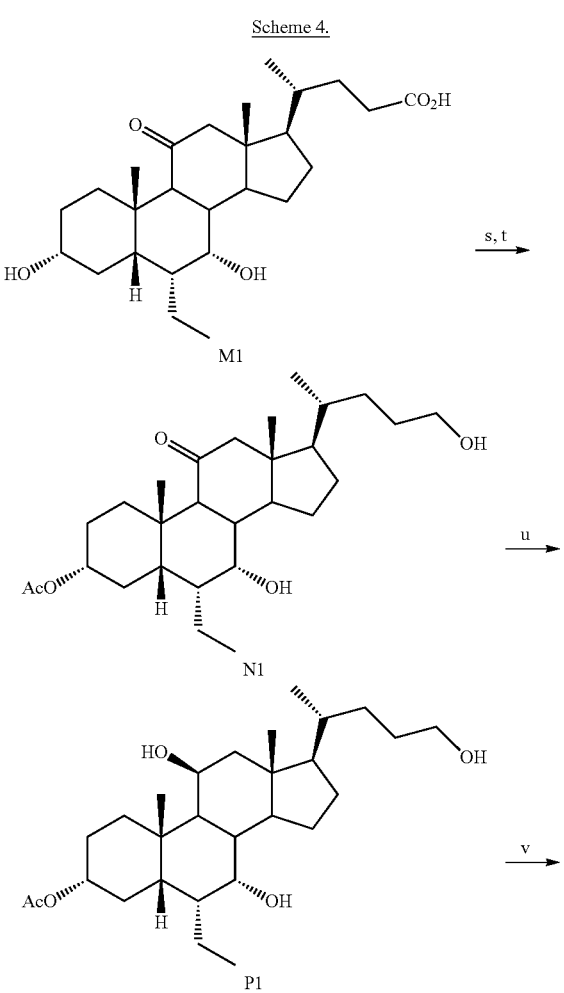

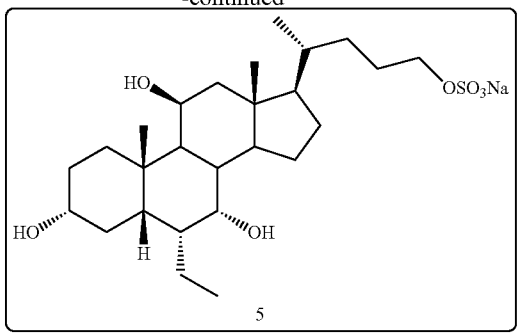

Scheme 4. Reagents and conditions: s) Ac₂O, NaHCO₃, THF, reflux; t) Et₃N, ClCO₂Et, THF, r.t.; NaBH₄, THF, H₂O; u) NaBH₄, THF, H₂O; and v) PyrSO₃, pyridine; NaOH, MeOH, H₂O.

3α-Acetoxy-7α-hydroxy-11-oxo-6α-ethyl-5β-cholan-24-ol (Compound N1)

To a solution of Compound M1 (120 mg, 0.27 mmol) in freshly distilled THF (4 mL), NaHCO₃ (417 mg, 4.97 mmol) and Ac₂O (0.47 mL, 4.97 mmol) were added and the suspension was refluxed for 24 h under argon atmosphere. The mixture was cooled to room temperature, treated with aqueous HCl and extracted with EtOAc (3×10 mL). The collected organic phases were sequentially washed with aqueous HCl, water, a saturated solution of NaHCO₃, brine, and dried over anhydrous Na₂SO₄. After being concentrated under reduced pressure, the crude was dissolved in freshly distilled THF (3 mL), treated with Et₃N (0.22 mL, 1.54 mmol) and ClCO₂Et (0.14 mL, 1.45 mmol) and the mixture was allowed to react at room temperature for 2 h under argon atmosphere. The suspension was filtered and the filtrate treated with a suspension of NaBH₄ (125 mg, 3.30 mmol) in H₂O (1 mL) and stirred for 3 h. The mixture was acidified with aqueous HCl and extracted with EtOAc (3×10 mL). The combined organic layers were washed with H₂O, brine, dried over anhydrous Na₂SO₄, and concentrated under vacuum. The crude was purified by flash chromatography thus obtaining Compound N1 (70 mg, 0.15 mmol).

3α-Acetoxy-7α,11β-dihydroxy-6α-ethyl-5β-cholan-24-ol (Compound P1)

To a solution of Compound N1 (0.15 mmol) in a binary mixture of THF and H₂O, NaBH₄ (3.75 mmol) was added and the mixture was stirred at room temperature for 24 h. The suspension was treated with aqueous HCl and extracted with EtOAc (3×10 mL). The collected organic phases were washed with H₂O, brine, dried over anhydrous Na₂SO₄, and concentrated under reduced pressure giving Compound P1 in quantitative yield.

3α,7α,11β-Trihydroxy-6α-ethyl-5β-cholan-24-O-sulphate, sodium salt (Compound 5)

PyrSO₃ (48 mg, 0.30 mmol) was added to a solution of Compound P1 (70 mg, 0.15 mmol) in pyridine (2.7 mL) and allowed to react at room temperature for 30 h under argon atmosphere. Pyridine was removed under vacuum and the residue stirred with a solution of NaOH (60 mg, 1.5 mmol) in a mixture of MeOH and H₂O for 3 d. The mixture was concentrated under reduced pressure to evaporate MeOH, diluted with H₂O (2 mL), and washed with Et₂O (3×10 mL). The aqueous alkaline phase was filtered on a reverse phase RP-18 pad to obtain Compound 5 (47 mg, 0.085 mmol, 57% yield) as pure white solid.

Compound 5: ¹H-NMR (400 MHz, CD₃OD): δ 0.88-0.92 (6H, m, CH₃-18, CH₃-26), 1.00 (3H, d, J=6.3 Hz, CH₃-21), 1.14 (3H, s, CH₃-19), 3.32-3.35 (1H, brm, CH-3), 3.72 (1H, brs, CH-7), 3.94-3.97 (2H, brm, CH₂-24), 4.20 (1H, brs, CH-11). ¹³C-NMR (400 MHz, CD₃OD): 12.1, 14.7, 19.1, 23.6, 24.7, 27.1, 27.7, 29.1, 31.9, 33.1, 34.8, 36.4, 36.9, 37.0, 38.3 (×2), 42.6, 42.7, 49.5, 50.1, 52.2, 58.0, 69.1, 69.7, 71.4, 73.3.

Example 6

Synthesis of 3α,7α,11β-trihydroxy-6α-ethyl-22-(1,2,4-oxadiazol-5-oxo-3-yl)-23,24-bisnor-5β-cholane (Compound 6)

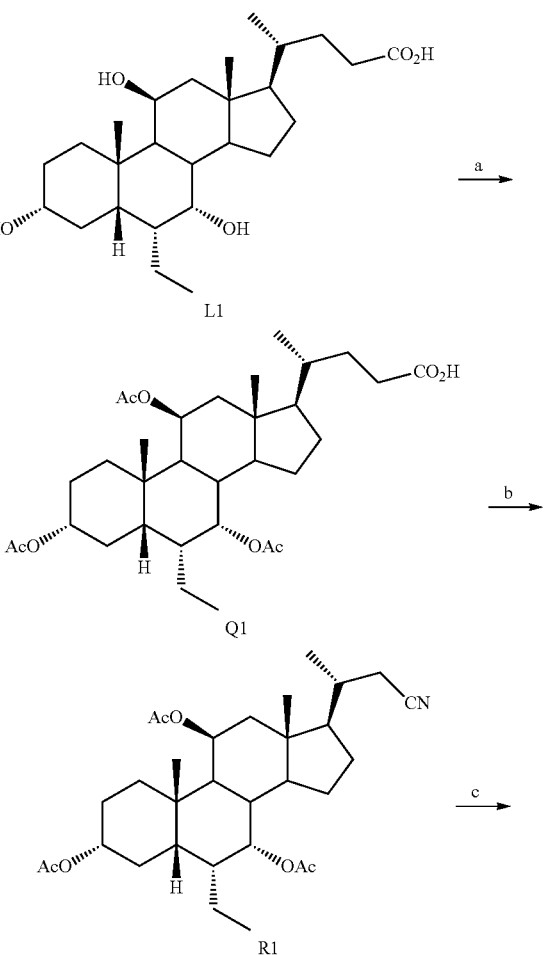

Scheme 5.

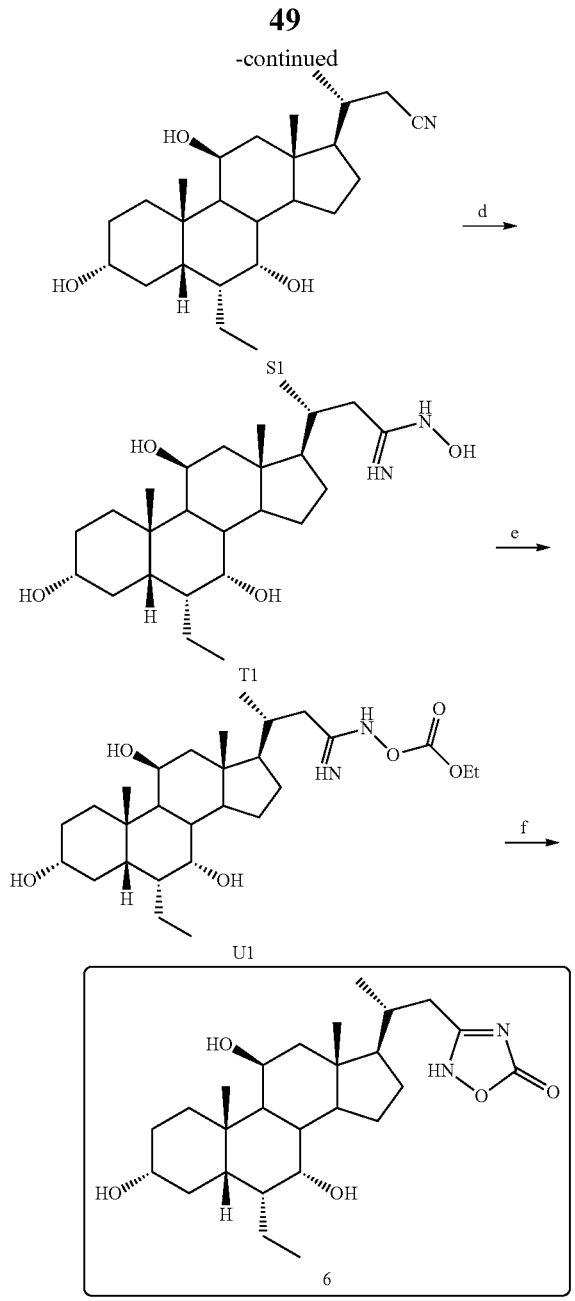

Scheme 5. Reagents and conditions: a) Ac$_2$O, Bi(OTf)$_3$, CH$_2$Cl$_2$; b) TFAA, NaNO$_2$, TFA; c) NaOH, MeOH; d) NH$_2$OH·HCl, Na$_2$CO$_3$·10H$_2$O, EtOH; e) ClCO$_2$Et, pyridine, THF; f) pyridine, toluene.

3α,7α,11β-Triacetoxy-6α-ethyl-5β-cholan-24-oic acid (Compound Q1)

To a suspension of Compound L1 (660 mg, 1.5 mmol) in CH$_2$Cl$_2$ (15 mL), Ac$_2$O (22.7 mmol) and Bi(OTf)$_3$ (0.08 mmol) were added and the mixture was stirred at room temperature for 1 h. The reaction mixture was filtered and the filtrate treated with HCl 37%. The organic phase was washed with H$_2$O, with a saturated solution of NaHCO$_3$ and brine, dried over anhydrous Na$_2$SO$_4$ and concentrated under reduced pressure to obtain Q1 (820 mg, 1.46 mmol, 96% yield), which was used for the next step without further purification.

Compound Q1: $^1$H-NMR (400 MHz, CDCl$_3$): δ 0.76 (3H, s, CH$_3$-18), 0.87-0.90 (6H, m, CH$_3$-21, CH$_3$-26), 1.04 (3H, s, CH$_3$-19), 2.03-2.05 (6H, m, OCOCH$_3$ ×2), 2.08 (3H, s, OCOCH$_3$), 4.52-4.61 (1H, m, CH-3), 5.20 (1H, s, CH-7), 5.25 (1H, s, CH-11).

3α,7α,11β-Triacetoxy-6α-ethyl-24-nor-5β-cholan-23-nitrile (Compound R1)

A suspension of Compound Q1 (820 mg, 1.46 mmol) in TFA (4.6 mL) at 0° C. was treated with TFAA (1.55 mL) and stirred at 0° C. for 45 min. NaNO$_2$ (4.4 mmol) was added and the mixture was reacted at 0° C. for 45 min and at 50° C. for additional 45 min. The reaction mixture was cooled to room temperature and poured into crushed ice. The aqueous phase was filtered under vacuum and the resulting orange-yellow solid was dissolved in EtOAc (30 mL), washed with a saturated solution of NaHCO$_3$, H$_2$O and brine. The organic layer was dried over anhydrous Na$_2$SO$_4$, concentrated under reduced pressure and to obtain Compound R1 (770 mg) as a crude that was used for the next step without further purification.

Compound R1: $^1$H-NMR (400 MHz, CDCl$_3$): δ 0.76 (3H, s, CH$_3$-18), 0.84-0.87 (3H, m, CH$_3$-25), 1.02 (3H, s, CH$_3$-19), 1.08 (3H, d, J=6.4 Hz, CH$_3$-21), 2.01 (6H, brs, OCOCH$_3$ ×2), 2.07 (3H, s, OCOCH$_3$), 4.52-4.61 (1H, m, CH-3), 5.18 (1H, s, CH-7), 5.24 (1H, s, CH-11).

3α,7α,11β-Trihydroxy-6α-ethyl-24-nor-5β-cholan-23-nitrile (Compound S1)

Compound R1 (770 mg) was dissolved in MeOH (10 mL) and refluxed for 3 d with NaOH (1.2 g). After solvent removal, the residue was dissolved in CHCl$_3$ (30 mL) and treated with 1 N HCl. The aqueous phase was extracted with CHCl$_3$ and the combined organic layers were washed with H$_2$O and brine, dried over anhydrous Na$_2$SO$_4$ and concentrated under reduced pressure. The crude was purified by silica gel flash chromatography using CH$_2$Cl$_2$ and MeOH as eluting solvents to obtain Compound S1 (180 mg, 0.445 mmol) in high purity grade.

Compound S1: $^1$H-NMR (400 MHz, CDCl$_3$): δ 0.87-0.91 (6H, m, CH$_3$-18, CH$_3$-25), 1.13 (3H, s, CH$_3$-19), 1.17 (3H, d, J=6.5 Hz, CH$_3$-21), 3.42-3.50 (1H, m, CH-3), 3.77 (1H, s, CH-7), 4.28 (1H, s, CH-11).

3α,7α,11β-Trihydroxy-6α-ethyl-24-nor-N-hydroxy-5β-cholan-23-amidine (Compound T1)

NH$_2$OH.HCl (557 mg) and Na$_2$CO$_3$.10H$_2$O (2.30 g) were added to a solution of Compound S1 (180 mg, 0.445 mmol) in EtOH (8 mL) and the resulting mixture was refluxed for 2 d. The suspension was cooled to room temperature and filtered under vacuum. The solid was washed with EtOAc and the organic phase was washed with H$_2$O, brine, dried over anhydrous Na$_2$SO$_4$ and concentrated under reduced pressure. The crude, containing the desired intermediate Compound T1, was used for the next step without further purification.

Compound T1: $^1$H-NMR (400 MHz, CD$_3$OD): δ 0.90 (3H, t, J=7.3 Hz, CH$_3$-25), 0.96-0.98 (6H, m, CH$_3$-18, CH$_3$-21), 1.14 (3H, s, CH$_3$-19), 3.31-3.40 (1H, m, CH-3), 3.72 (1H, s, CH-7), 4.20 (1H, s, CH-11).

3α,7α,11β-Trihydroxy-6α-ethyl-24-nor-N-[(ethoxycarbonyl)oxy]-5β-cholan-23-amidine (Compound U1)

To a solution of Compound T1, (180 mg) in THF (2 mL) and pyridine (50 μL, 0.6 mmol) cooled at 0° C., a solution of ClCO$_2$Et (0.45 mmol) in THF (1 mL) was added dropwise and the resulting suspension was stirred under argon atmosphere for 30 min. The mixture was treated with H$_2$O and extracted with EtOAc (3×10 mL). The collected organic phases were washed with brine, dried over anhydrous Na$_2$SO$_4$, concentrated under vacuum to provide Compound U1, which was used for the next step without further purification.

Compound U1: $^1$H-NMR (400 MHz, CDCl$_3$): δ 0.86-0.92 (6H, m, CH$_3$-25, CO$_2$CH$_2$CH$_3$), 1.00 (3H, d, J=6.1 Hz, CH$_3$-21), 1.11 (3H, s, CH$_3$-18), 1.23 (3H, s, CH$_3$-19), 3.35-3.44 (1H, m, CH-3), 3.77 (1H, s, CH-7), 4.13-4.39 (3H, m, CH-11, CO$_2$CH$_2$CH$_3$), 4.90-5.05 (1H, m, NH).

3α,7α,11β-Trihydroxy-6α-ethyl-22-(1,2,4-oxadiazol-5-oxo-3-yl)-23,24-bisnor-5β-cholane (Compound 6)

Compound U1 (210 mg, 0.412 mmol) was dissolved in toluene (6 mL) and pyridine (0.6 mL) and refluxed under argon atmosphere for 20 h. After being cooled to room temperature, the mixture was diluted with EtOAc (10 mL) and washed with 1 N HCl, H$_2$O, a saturated solution of NaHCO$_3$ and brine. The organic layer was dried over anhydrous Na$_2$SO$_4$, concentrated under reduced pressure and purified to obtain Compound 6 (35 mg, 0.076 mmol).

Compound 6: $^1$H-NMR (400 MHz, CD$_3$OD): δ 0.89-0.93 (3H, t, J=7.3 Hz, CH$_3$-24), 0.96-0.99 (6H, m, CH$_3$-18, CH$_3$-21), 1.15 (3H, s, CH$_3$-19), 2.09 (1H, d, J=14.1 Hz), 2.37 (1H, d, J=12.3 Hz), 2.57 (1H, d, J=13.4 Hz), 3.31-3.40 (1H, m, CH-3), 3.66 (1H, s, OH), 3.73 (1H, s, CH-7), 4.21 (1H, s, CH-11). $^{13}$C-NMR (100.6 MHz, CD$_3$OD): δ 12.0, 14.7, 19.2, 23.5, 24.7, 27.6, 29.1, 31.9, 34.5, 34.7, 36.1, 36.4, 36.9, 38.2 (×2), 42.6, 43.0, 49.4, 49.9, 52.2, 58.4, 68.9, 71.3, 73.3, 169.3, 173.0.

Example 7

Synthesis of 3α,7α,11β-trihydroxy-6α-ethyl-23-(1,2,4-oxadiazol-5-oxo-3-yl)-23-nor-5β-cholane (Compound 7)

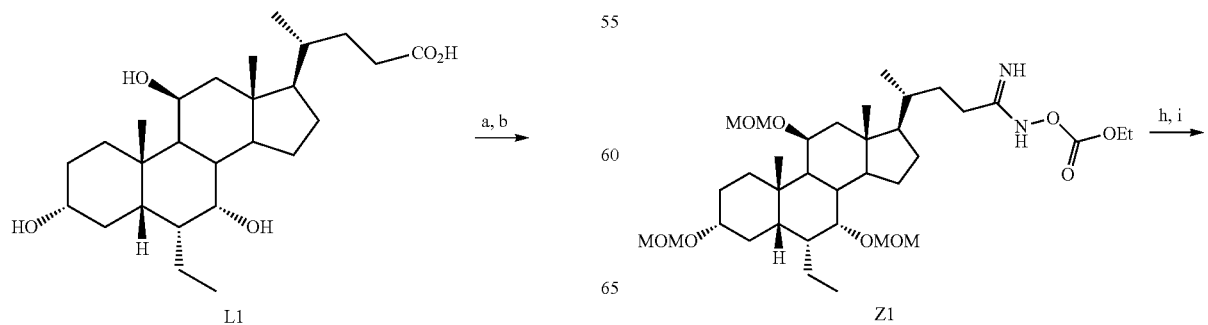

-continued

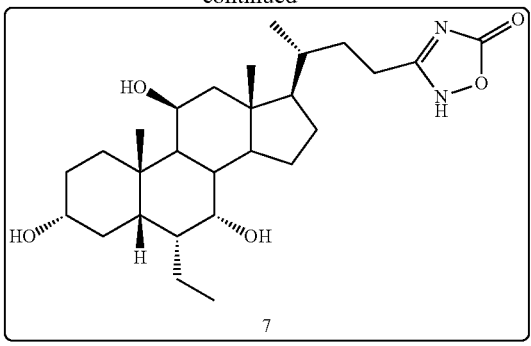

Scheme 6. Reagents and conditions: a) MeOH, p-TSA, ultrasounds; b) MOMCl, DIPEA, DMAP, CH$_2$Cl$_2$; c) NaOH, MeOH; d) ClCO$_2$iBu, Et$_3$N, THF, NH$_4$OH 30%; e) CNCl, DMF; f) NH$_2$OH·HCl, Na$_2$CO$_3$·10 H$_2$O, EtOH; g) ClCO$_2$Et, pyridine, THF; h) pyridine, toluene; i) HCl 3 N, acetone.

Methyl 6α-ethyl-3α,7α,11β-trimethoxymethyloxy-5β-cholan-24-oate (Compound V1)

A solution of Compound L1 (730 mg, 1.7 mmol) and p-TSA (0.17 mmol) in MeOH (10 mL) was treated under ultrasounds for 3 h. The solvent was removed, the residue dissolved in EtOAc (10 mL) and washed with a saturated solution of NaHCO$_3$. The aqueous phase was extracted with EtOAc (2×10 mL) and the combined organic layers washed with brine, dried over anhydrous Na$_2$SO$_4$ and concentrated under vacuum. The crude (700 mg, 1.55 mmol) was dissolved in CH$_2$Cl$_2$ (20 mL) and refluxed with DIPEA (18.6 mmol), DMAP (0.16 mmol) and MOMCl (15.5 mmol) for 3 d. The mixture was cooled to room temperature and sequentially washed with a saturated solution of NH$_4$Cl$_1$, H$_2$O and brine. The organic phase was dried over anhydrous Na$_2$SO$_4$, concentrated under reduced pressure and the obtained crude Compound VI which was used for the next step without further purification.

Compound V1: $^1$H-NMR (400 MHz, CDCl$_3$): δ 0.81 (3H, s, CH$_3$-18), 0.85-0.89 (3H, m, CH$_3$-26), 0.93 (3H, d, J=6.2 Hz, CH$_3$-21), 1.10 (3H, s, CH$_3$-19), 3.34-3.40 (10H, m, CH-3, OCH$_2$OCH$_3$ ×3), 3.53 (1H, s, CH-7), 3.65 (3H, s, CO$_2$CH$_3$), 3.93 (1H, s, CH-11), 4.55-4.70 (6H, m, OCH$_2$OCH$_3$ ×3).

6α-Ethyl-3α,7α,11β-trimethoxymethyloxy-5β-cholan-24-amide (Compound W1)

To a solution of Compound V1 (980 mg, 1.6 mmol) in MeOH (10 mL), NaOH (15.5 mmol) was added and the mixture was allowed to react at 50° C. The solvent was removed under vacuum, the residue dissolved in H$_2$O (5 mL) and treated with HCl 1 N. The suspension was extracted with CHCl$_3$ (3×10 mL) and the combined organic phases were washed with H$_2$O and brine, dried over anhydrous Na$_2$SO$_4$ and concentrated under reduced pressure. The crude (840 mg) was dissolved in freshly distilled THF (18 mL), cooled at 0° C. and stirred with Et$_3$N (0.288 mL) and ClCO$_2$iBu (0.250 mL) for 20 min under argon atmosphere. NH$_4$OH 30% (0.28 mL) was added and the resulting suspension was reacted for 40 min at room temperature. The mixture was treated with H$_2$O and extracted with EtOAc (3×10 mL). The collected organic phases were washed with HCl 1 N, H$_2$O, a saturated solution of NaHCO$_3$, H$_2$O and brine, dried over anhydrous Na$_2$SO$_4$, and concentrated under reduced pressure to obtain Compound W1 (900 mg) that was used for the next step without further purification.

Compound W1: $^1$H-NMR (400 MHz, CDCl$_3$): δ 0.62-0.82 (9H, m, CH$_3$-18, CH$_3$-21, CH$_3$-26), 0.99 (3H, s, CH$_3$-19), 3.22-3.30 (10H, m, CH-3, OCH$_2$OCH$_3$ ×3), 3.42 (1H, s, CH-7), 3.82 (1H, s, CH-11), 4.46-4.57 (6H, m, OCH$_2$OCH$_3$ ×3), 6.03 (1H, brs, CONH$_2$), 6.27 (1H, brs, CONH$_2$).

6α-Ethyl-3α,7α,11β-trimethoxymethyloxy-5β-cholan-24-nitrile (Compound X1)

A solution of Compound W1 (890 mg) and CNCl (578 mg) in DMF (22 mL) was stirred at room temperature under argon atmosphere for 12 h. The resulting suspension was diluted with EtOAc (50 mL) and washed with H$_2$O (3×15 mL). The organic layer was washed with brine, dried over anhydrous Na$_2$SO$_4$ and concentrated under reduced pressure. The crude was purified by flash chromatography on silica gel by using PET-EtOAc as eluting solvent system to obtain Compound X1 as a pale yellow oil (260 mg, 0.473 mmol).

Compound X1: $^1$H-NMIR (400 MHz, CDCl$_3$): δ 0.83-0.88 (6H, m, CH$_3$-18, CH$_3$-26), 0.95 (3H, d, J=6.0 Hz, CH$_3$-21), 1.05 (3H, s, CH$_3$-19), 3.33-3.40 (10H, m, CH-3, OCH$_2$OCH$_3$ ×3), 3.52 (1H, s, CH-7), 3.91 (1H, s, CH-11), 4.55-4.69 (6H, m, OCH$_2$OCH$_3$ ×3).

6α-Ethyl-3α,7α,11β-trimethoxymethyloxy-N-hydroxy-5β-cholan-24-amidine (Compound Y1)

NH$_2$OH.HCl (386 mg) and Na$_2$CO$_3$. (1.6 g) were added to a solution of Compound X1 (170 mg, 0.309 mmol) in EtOH (6 mL) and refluxed till starting material consumption. The suspension was cooled to room temperature and filtered under vacuum. The remaining solid was washed with EtOAc (15 mL) and the filtered organic phase was washed with H$_2$O, brine, dried over anhydrous Na$_2$SO$_4$ and concentrated under reduced pressure. The crude, containing the desired intermediate Compound Y1, was used for the next step without further purification.

Compound Y1: $^1$H-NMR (400 MHz, CDCl$_3$): δ 0.77 (3H, s, CH$_3$-18), 0.81-0.84 (3H, t, J=6.8 Hz, CH$_3$-26), 0.90 (3H, d, J=6.2 Hz, CH$_3$-21), 1.05 (3H, s, CH$_3$-19), 3.30-3.36 (10H, m, CH-3, OCH$_2$OCH$_3$ ×3), 3.48 (1H, s, CH-7), 3.88 (1H, s, CH-11), 4.51-4.65 (6H, m, OCH$_2$OCH$_3$ ×3), 4.76 (2H, brs, NH, NH—OH).

6α-Ethyl-3α,7α,11α-trimethoxymethyloxy-N-[(ethoxycarbonyl)oxy]-5β-cholan-24-amidine (Compound Z1)

To a solution of Compound Y1 (200 mg) in THF (2 mL) and pyridine (0.46 mmol) cooled at 0° C., a solution of ClCO$_2$Et (0.34 mmol) in THF (1 mL) was added dropwise and the resulting suspension was stirred under argon atmosphere for 30 min. The mixture was treated with H$_2$O and extracted with EtOAc (3×10 mL). The collected organic phases were washed with brine, dried over anhydrous Na$_2$SO$_4$, concentrated under vacuum to provide Compound Z1, which was used for the next step without further purification.

Compound Z1: $^1$H-NMR (400 MHz, CDCl$_3$): δ 0.77 (3H, s, CH$_3$-18), 0.81-0.84 (3H, t, J=6.8 Hz, CH$_3$-26), 0.92 (3H, d, J=6.1 Hz, CH$_3$-21), 1.05 (3H, s, CH$_3$-19), 1.27 (3H, t, J=7.0 Hz, OCH$_2$CH$_3$), 3.30-3.36 (10H, m, CH-3, OCH$_2$OCH$_3$ ×3), 3.48 (1H, s, CH-7), 3.88 (1H, s, CH-11), 4.21 (2H, q, J=7.0 Hz, OCH$_2$CH$_3$), 4.51-4.65 (6H, m, OCH$_2$OCH$_3$ ×3), 4.88 (2H, brm, NH, NH—OH).

3α,7α,11β-Trihydroxy-6α-ethyl-23-(1,2,4-oxadiazol-5-oxo-3-yl)-24-nor-5β-cholane (Compound 7)

Compound Z1 (200 mg) obtained from the previous step was dissolved in toluene (5 mL) and pyridine (0.5 mL), refluxed under argon atmosphere for 8 h, and stirred at room temperature for additional 12 h. The mixture was diluted with EtOAc (10 mL) and sequentially washed with HCl 1 N, $H_2O$, a saturated solution of $NaHCO_3$ and brine. The organic layer was dried over anhydrous $Na_2SO_4$ and concentrated under reduced pressure. The resulting crude was dissolved in acetone (15 mL) and stirred with HCl 3 N (1.5 mL) at 40° C. for 6 h. The mixture was diluted with $H_2O$ and the organic layer was concentrated under reduced pressure. The aqueous phase was then extracted with EtOAc (3×10 mL) and the combined organic layers treated with a saturated solution of $NaHCO_3$, washed with brine, dried over anhydrous $Na_2SO_4$ and concentrated under vacuum. The crude was purified by flash chromatography to yield Compound 7 (29.6 mg, 0.062 mmol) as a white solid.

Compound 7: $^1$H-NMR (400 MHz, $CD_3OD$): δ 0.89-0.93 (6H, m, $CH_3$-18, $CH_3$-25), 1.05 (3H, d, J=6.3 Hz, $CH_3$-21), 1.15 (3H, s, $CH_3$-19), 2.07-2.11 (1H, m), 2.20-2.24 (1H, m), 2.45-2.50 (1H, m, CH-23), 2.58-2.68 (1H, m, CH-23), 3.32-3.36 (1H, m, CH-3), 3.73 (1H, s, CH-7), 4.20 (1H, s, CH-11). $^{13}$C-NMR (100.6 MHz, $CD_3OD$): 12.0, 14.6, 18.7, 23.0, 23.5, 24.7, 27.7, 29.1, 30.8, 31.9, 33.1, 34.7, 36.4, 36.8, 36.9, 38.3 (×2), 42.6, 42.8, 50.0, 52.2, 57.6, 69.0, 71.4, 73.3, 162.2, 162.8.

Example 6

FXR/TGR5 Activity of the Compounds 1-7

In the nucleus, ligand-bound nuclear receptors (NRs) modulate initiation of transcription by directly interacting with the basal transcriptional machinery or by contacting bridging factors called coactivators (Onate, et al., Science, 1995, 270, 1354-1357; Wang, et al., J Biol Chem, 1998, 273, 30847-30850; and Zhu, et al., Gene Expr, 1996, 6, 185-195). The ligand-dependent interaction of NRs with their coactivators occurs between activation function 2 (AF-2), located in the receptor ligand-binding domain (LBD) and the nuclear receptor boxes (NR box), located on the coactivators (Nolte, et al., Nature, 1998, 395, 137-143). Several lines of evidence have demonstrated that the LXXLL peptide sequence present in the NR box represents a signature motif that facilitates the interaction of different proteins with the AF-2 region (Heery, et al., Nature, 1997, 387, 733-736; and Torchia, et al., Nature, 1997, 387, 677-684).

AlphaScreen was used with the aim of identifying novel modulators by taking advantage of the bimolecular interaction prevailing between FXR and the LXXLL motif present in the NR box of the steroid receptor coactivator 1 (SRC-1).

Human FXR-LBD-GST was incubated with increasing concentrations of the indicated ligands in the presence of biotinylated LXXLL SRC-1 peptide. The AlphaScreen signal increases when the complex receptor-coactivator is formed. The compounds of this invention are potent FXR agonists. Data are provided in Tables 1 and 2.

Bile acids (BAs) modulate not only several nuclear hormone receptors, but are also agonists for the G protein-coupled receptor (GPCR) TGR5 (Makishima, et al., Science, 1999, 284, 1362-1365; Parks, et al., Science, 1999, 284, 1365-1368; Maruyama, et al., Biochem Biophys Res Commun, 2002, 298, 714-719; and Kawamata, et al., J Biol Chem, 2003, 278, 9435-9440). Signalling via FXR and TGR5 modulates several metabolic pathways, regulating not only BA synthesis and enterohepatic recirculation, but also triglyceride, cholesterol, glucose, and energy homeostasis.

To evaluate the capacity of a compound of the invention to activate TGR5, the compound of the invention and other comparison compounds were screened for an increase of intracellular cAMP as a read-out for TGR5 activation. Human enteroendocrine $NCI-H_{716}$ cells constitutively expressing TGR5 were exposed to increasing concentrations of a compound of the invention, and intracellular cAMP levels were measured by TR-FRET. Lithocholic acid (LCA) was used as positive control. The compounds of this invention show high selectivity for FXR over TGR5. Data are provided in

TABLE 1

FXR/TGR5 Activity of Compounds 1-5

| Compound | AlphaScreen Assay Human FXR Ref CDCA = 15 ± 3 μM | HTR-FRET (cAMP) Human TGR5 (NCI-H716 cells) Ref LCA = 7 ± 3 μM |
|---|---|---|
| Compound 1 | 0.68 | >100 |
| Compound 2 | 0.23 | 93 |
| Compound 3 | 0.0075 ± 0.0005 | 83 ± 7 |
| Compound 4 | 0.264 ± 0.016 | 13.7 ± 2.3 |
| Compound 5 | 0.015 ± 0.004 | 78 ± 1 |
| Compound A | 0.2 ± 0.018 | 15 ± 5 |
| Compound B | 0.03 | 0.63 |
| Compound C | 175 | 0.9 |

TABLE 2

FXR/TGR5 Activity of Compounds L1, 3, 5, 6, and 7

| Compound | AlphaScreen Human FXR $EC_{50}$ (μM) | HTR-FRET (cAMP) Human TGR5 $EC_{50}$ (μM) |
|---|---|---|
| L1 | 0.15 ± 0.5 | No activity |
| Compound 3 | 0.0075 ± 0.0005 | 83 ± 7 |
| Compound 5 | 0.015 ± 0.004 | 78 ± 1 |
| Compound 6 | 0.042 ± 0.002 | No activity |
| Compound 7 | 0.029 ± 0.005 | No activity |

TABLE 3

FXR agonist activity across human, mouse, rat, and dog orthologs

| Compound | AlphaScreen hFXR $EC_{50}$ (μM) | AlphaScreen mFXR $EC_{50}$ (μM) | AlphaScreen rFXR $EC_{50}$ (μM) | AlphaScreen dFXR $EC_{50}$ (μM) |
|---|---|---|---|---|
| L1 | 0.15 ± 0.5 | 0.99 ± 0.05 | 1.0 ± 0.03 | 4 ± 1 |
| Compound 3 | 0.0075 ± 0.0005 | 0.25 ± 0.04 | 0.13 ± 0.01 | 0.9 ± 0.1 |
| Compound 5 | 0.015 ± 0.004 | 0.12 ± 0.02 | 0.14 ± 0.02 | 0.73 ± 0.01 |
| Compound 6 | 0.042 ± 0.002 | 0.27 ± 0.02 | 0.24 ± 0.01 | 0.8 ± 0.1 |
| Compound 7 | 0.029 ± 0.005 | 0.21 ± 0.01 | 0.2 ± 0.01 | 0.7 ± 0.01 |

TABLE 4

Cross species TGR5 activity

| Compound | hTGR5 CHO $EC_{50}$ (μM) | mTGR5 CHO $EC_{50}$ (μM) | rTGR5 CHO $EC_{50}$ (μM) | dTGR5 CHO $EC_{50}$ (μM) |
|---|---|---|---|---|
| L1 | No activity | No activity | No activity | No activity |
| Compound 3 | 5 ± 1 | 3 ± 0.5 | No activity | No activity |
| Compound 5 | 3 ± 1 | 4 ± 1 | No activity | No activity |
| Compound 6 | No activity | No activity | No activity | 1.5 ± 0.3 |
| Compound 7 | No activity | 9.5 ± 2 | No activity | 7.6 ± 0.01 |

Example 7

Nuclear Receptor Selectivity Profile

Using the AlphaScreen assay, the selectivity of a compound of the invention against the following nuclear receptors involved in the metabolic pathways can be evaluated: LXRP, PXR, CAR, PPARα, PPARα, PPARγ, RAR, RARα, VDR, TR, PR, RXR, GR, and ER.

Compounds L1, 3, 5, 6 and 7 were tested against the panel of available nuclear receptor in both agonist and antagonist mode. Neither compound activated any of the receptors in agonist (dose response to 200 µM) or antagonist mode (fixed concentration at 10 µM).

Example 8

FXR Target Gene Panel

To evaluate the capacity of a compound of the invention to modulate FXR target genes, quantitative RT-PCR assays are performed. HepG2 cells are selected as a relevant cell line to determine whether a compound of the invention can regulate the endogenous FXR genetic network. The ability of a compound of the invention to induce FXR target genes is assessed by isolating total RNA from cells treated overnight with 1 µM of compounds A, B, and a compound of the invention. Compound A is established as a potent FXR selective agonist and compound B is established as a dual potent FXR/TGR5 agonist.

FXR regulates the expression of several target genes involved in BA homeostasis. Briefly, FXR plays a central role in several metabolic pathways, including i.e., lipid metabolism, bile-acids metabolism, and carbohydrate metabolism. Regarding gene expression profiling, the genes encoding proteins involved in lipid metabolism include, e.g., APOCII, APOE, APOAI, SREBP-1C, VLDL-R, PLTP, and LPL; the genes encoding proteins involved in bile-acids metabolism include, e.g., OSTα/β, BSEP, MRP2, SHP, CYP7A1, FGF19, SULT2A1, and UGT2B4; and the genes encoding proteins involved in carbohydrate metabolism include, e.g., PGCla, PEPCK, and GLUT2. FXR target genes: BSEP, SHP, OSTβ and CYP7A1 were evaluated following stimulation of Compounds 3, 5, 6, and 7 on HepG2 cells for 18 hours. Compound L1 was used as a control. Compounds 3, 5, 6, and 7 significantly bind to FXR in hepatic cells modulating FXR target genes.

Example 9

In-Vitro Cytotoxicity

To evaluate in-vitro cytotoxicity of a compound of the invention, two different assay methods are employed. The assays evaluate cell viability by measuring ATP levels and cytotoxicity by measuring LDH release. Adenosine Triphosphate (ATP) nucleotide represents the source of energy at the basic molecular level, as it is a multifunctional molecule that is used in every cell as a coenzyme and is an integral part of the mitochondrial DNA (Kangas, et al., Medical Biology, 1984, 62, 338-343; Crouch, et al., J Immunol. Methods, 1993, 160, 81-88; and Petty, et al., J Biolumin. Chemilumin. 1995, 10, 29-34). It has been called the "molecular unit of currency" when it comes to intracellular energy transfer. This is to ensure the important role of ATP in metabolism and a drop in ATP content is the first step in revealing cellular damage (Storer, et al., Mutation Research, 1996, 368, 59-101; and Cree and Andreotti, Toxicology In-Vitro, 1997, 11, 553-556).

An additional method to determine the viability of cells is to detect the integrity of the membrane that defines the cellular compartmentalization. Measuring the leakage of components out of the cytoplasm, in damaged cell membranes, indicates loss of membrane integrity, and LDH release is the method used to determine common toxicity in cells. HepG2 cells are treated with a compound of the invention, and serial dilutions are performed. LCA dilutions are added to the plated cells as assay controls together with no-cell and untreated cells. The assay is performed in triplicate for each test compound concentration.

Cell viability was determined as a measure of intracellular ATP related to the time of exposure and concentration of the test compounds (Sussman, Promega Cell Notes, Issue 3, 2002). Data are provided in Tables 5A and 5B.

TABLE 5A

In vitro Cytotoxicity of Compounds 3 and 5

| Compound | ATP Content $EC_{50}$ (µM) Ref Tamoxifen $EC_{50}$ 49 ± 9 µM |
|---|---|
| Compound 3 | No toxicity (100% living cells) |
| Compound 5 | No toxicity (100% living cells) |
| Compound A* | 230 |
| Compound B* | 800 |

* Rizzo et al., Mol. Pharm. 2010, 78, 617-630.

TABLE 5B

In vitro Cytotoxicity of Compounds 6 and 7 (LDH release and ATP content relative to Compounds 6 and 7 stimulation on HepG2.

| Compound | Membrane Integrity (LDH measure) $LC_{50}$ (µM) | ATP Content $EC_{50}$ (µM) |
|---|---|---|
| Tamoxifen | 35 ± 10 | 20 ± 5 |
| LCA | 100 ± 5 | 75 ± 5 |
| Compound 6 | No toxicity | No toxicity |
| Compound 7 | No toxicity | No toxicity |
| Compound L1 | No toxicity (100% living cells) | No toxicity |

Tamoxifen was used as a positive control of the assay and LCA was used as a reference.

Example 10

CYP4150 Screening

To evaluate the potential of a compound of the invention for drug-drug interactions, the six main CYP450 isoforms (CYP1A2, CYP2C9, CYP2C19, CYP2D6, CYP2E1, CYP3A4) are investigated (Obach, et al., J Pharmacol. Exp. Ther, 2006, 316, 336-348).

To determine interaction between a compound of the invention and cytochrome P450 enzymes, the compound of the invention is analyzed by its capacity to inhibit (or not) the production of a fluorescent signal, using recombinant CYP450 proteins (baculosomes; Invitrogen), substrates and inhibitors (Bidstrup, et al., Br J Clin. Pharmacol, 2003, 56, 305-14). As a positive control, a selective inhibitor for each CYP450 isoform is tested in the same plate.

TABLE 6

CYP450s Inhibition (test against the 6 major isozymes)

| CYP450 | Compound 3 IC$_{50}$ (µM) | Compound 5 IC$_{50}$ (µM) | Compound 6 IC$_{50}$ (µM) | Compound 7 IC$_{50}$ (µM) | Compound L1 IC$_{50}$ (µM) |
|---|---|---|---|---|---|
| CYP1A2 | >10 | >10 | >10 | >10 | >10 |
| CYP3A4 (Green substrate) | >10 | >10 | >10 | >10 | >10 |
| CYP3A4 (Blue substrate) | >10 | >10 | >10 | >10 | >10 |
| CYP2C9 | >10 | >10 | >10 | >10 | >10 |
| CYP2C19 | >10 | >10 | >10 | >10 | >10 |
| CYP2D6 | >10 | >10 | >10 | >10 | >10 |
| CYP2E1 | >10 | >10 | >10 | >10 | >10 |

Example 11

Human ERG Potassium Channel

To determine on channel function, the Predictor™ hERG Fluorescence Polarization assay is employed as it provides an efficient method for an initial determination of the propensity of test compounds to block the hERG channel (Dorn, et al, J Biomol. Screen, 2005, 10, 339-347). The assay is based on the assumption that the hERG potassium channel activity contributes to the resting membrane potential in permanently transfected cells, and thus a block of hERG channels should result in a depolarization of the cell membrane. The assay is designed to identify potential hERG channel blockers by producing data that accurately correlates with patch-clamp electrophysiology studies. Results from the Predictor™ assay demonstrate a high correlation with those obtained from patch clamp techniques (Dorn, et al., J Biomol Screen, 2005, 10, 339-347).

Membrane preparations from Chinese hamster ovary cells stably transfected with hERG potassium channel are used to evaluate the potential inhibitory effect of a compound of the invention on this channel using the Predictor™ fluorescence polarization assay. Reduction of membrane polarization as a result of inhibition of the hERG potassium channel is directly correlated with a reduction of the fluorescence polarization (FP).

The assay is performed in triplicate by using a 16-point dose-response of test compound and the positive controls E-4031 and Tamoxifen. An IC$_{50}$ of 15 nM (AmP=163) for E-4031 and 1,4 µM (ΔηιP=183) for Tamoxifen are obtained. An assay window more than 100 mP (millipolarization) is considered good. The non-linear regression curves are obtained by GraphPad Prism (GraphPad Software Inc.) analysis, to calculate the IC$_{50}$ values.

TABLE 7

Human ERG potassium channel inhibition

| Compound | hERG inhibition IC$_{50}$ (µM) |
|---|---|
| Compound 3 | >100 |
| Compound 5 | >100 |
| Compound 6 | >100 |
| Compound 7 | >100 |
| Compound L1 | >100 |

Compounds L1, 3, 5, 6 and 7 did not inhibit hERG potassium channel.

Example 12

Physiochemical Properties

Physiochemical properties of a compound of the invention such as water solubility, critical micellar concentration, surface tension, and LogP$_A$ were determined using methods known in the art. Data are provided in Table 8.

TABLE 8

Physiochemical Properties

| Bile Acid Derivative | CMC$^{(a)}$ (mM) | LogP$_{A-}^{(b)}$ |
|---|---|---|
| Compound 3 | 12.5 | 0.12 |
| Compound 5 | 8.5 | 0.61 |
| Compound 6 | 28 | 1.7 |
| Compound 7 | — | 2.0 |
| Compound L1 | 15.8 | 0.84 |
| Compound A | 2.9 | 2.5 |
| Compound B | 1.3 | 2.0 |
| Compound C | 2 | 1.4 |
| Compound D | — | 2.9 |
| Compound E | 5.9 | 1.6 |

$^{(a)}$CMC: Critical Micellar Concentration determined in 0.15 M NaCl water solution
$^{(b)}$LogP$_{A-}$: 1-octanol-water species partition coefficient of the studied bile acids as ionized species

The invention claimed is:

1. A compound selected from:

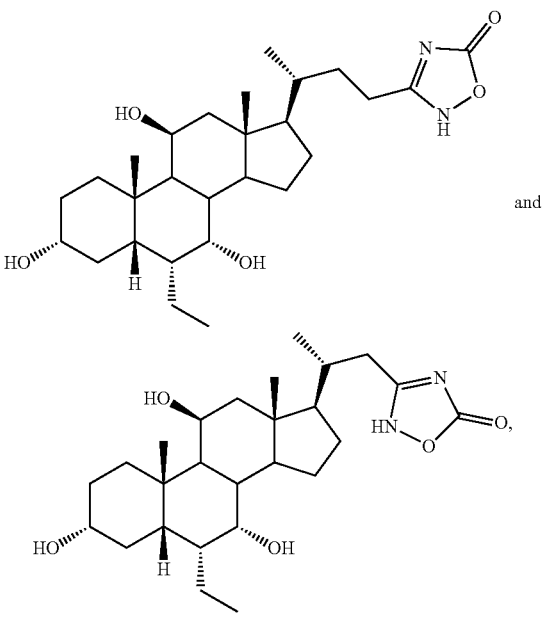

or a pharmaceutically acceptable salt or solvate thereof.

2. A pharmaceutical composition comprising the compound of claim 1 or a pharmaceutically acceptable salt or solvate thereof and a pharmaceutically acceptable carrier or excipient.

3. The compound of claim 1, which is

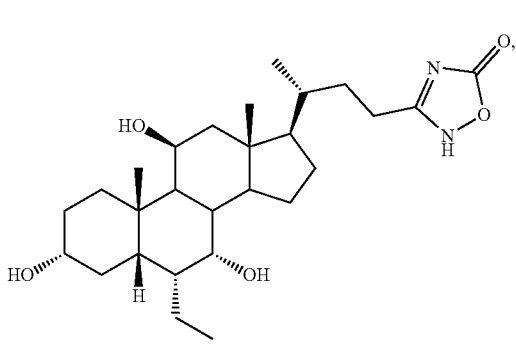 [SMILES: CC[C@H]1[C@@H](O)C2C3CC[C@H]([C@H](C)CCc4nc(=O)o[nH]4)[C@@]3(C)C[C@H](O)C2[C@@]2(C)CC[C@@H](O)C[C@@H]12]

or a pharmaceutically acceptable salt or solvate thereof.

4. The compound of claim 3, which is

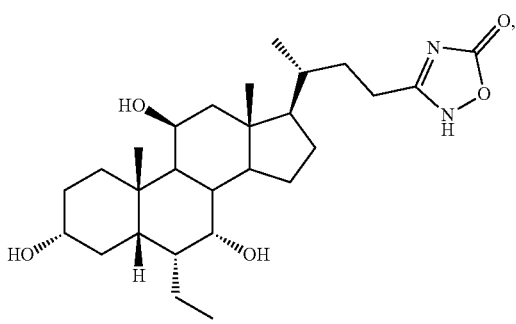 [SMILES: CC[C@H]1[C@@H](O)C2C3CC[C@H]([C@H](C)CCc4nc(=O)o[nH]4)[C@@]3(C)C[C@H](O)C2[C@@]2(C)CC[C@@H](O)C[C@@H]12]

or a pharmaceutically acceptable salt thereof.

5. The compound of claim 3, which is

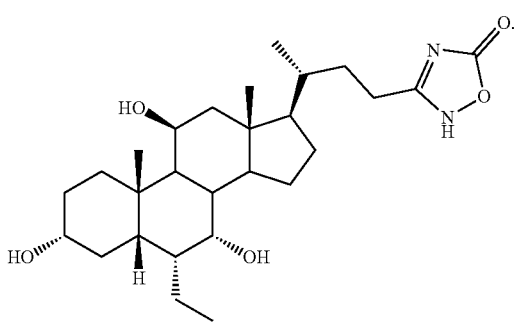 [SMILES: CC[C@H]1[C@@H](O)C2C3CC[C@H]([C@H](C)CCc4nc(=O)o[nH]4)[C@@]3(C)C[C@H](O)C2[C@@]2(C)CC[C@@H](O)C[C@@H]12]

6. The compound of claim 1, which is

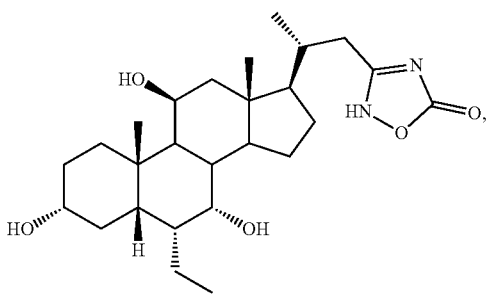 [SMILES: CC[C@H]1[C@@H](O)C2C3CC[C@H]([C@H](C)Cc4nc(=O)o[nH]4)[C@@]3(C)C[C@H](O)C2[C@@]2(C)CC[C@@H](O)C[C@@H]12]

or a pharmaceutically acceptable salt or solvate thereof.

7. The compound of claim 6, which is

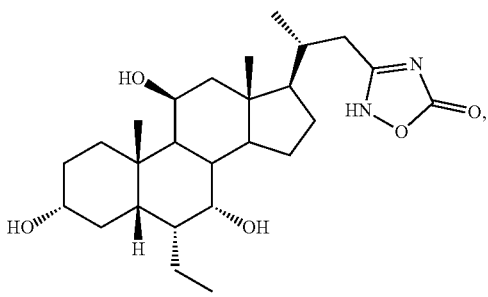 [SMILES: CC[C@H]1[C@@H](O)C2C3CC[C@H]([C@H](C)Cc4nc(=O)o[nH]4)[C@@]3(C)C[C@H](O)C2[C@@]2(C)CC[C@@H](O)C[C@@H]12]

or a pharmaceutically acceptable salt thereof.

8. The compound of claim 6, which is

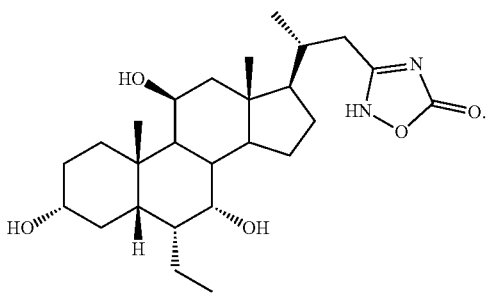 [SMILES: CC[C@H]1[C@@H](O)C2C3CC[C@H]([C@H](C)Cc4nc(=O)o[nH]4)[C@@]3(C)C[C@H](O)C2[C@@]2(C)CC[C@@H](O)C[C@@H]12]

9. A pharmaceutical composition comprising the compound of claim 3 or a pharmaceutically acceptable salt or solvate thereof and a pharmaceutically acceptable carrier or excipient.

10. A pharmaceutical composition comprising the compound of claim 6 or a pharmaceutically acceptable salt or solvate thereof and a pharmaceutically acceptable carrier or excipient.

* * * * *